(12) United States Patent
Kim et al.

(10) Patent No.: US 8,084,561 B2
(45) Date of Patent: Dec. 27, 2011

(54) PROCESS FOR PREPARING ACRYLATE COPOLYMERS

(75) Inventors: Son Nguyen Kim, Hemsbach (DE); Matthias Laubender, Schifferstadt (DE); Marianna Pierobon, Ludwigshafen (DE); Gabi Winter, Shanghai (CN)

(73) Assignee: BASF SE, Ludwigshafen (DE)

( * ) Notice: Subject to any disclaimer, the term of this patent is extended or adjusted under 35 U.S.C. 154(b) by 454 days.

(21) Appl. No.: 12/294,693

(22) PCT Filed: Mar. 23, 2007

(86) PCT No.: PCT/EP2007/052785
§ 371 (c)(1),
(2), (4) Date: Sep. 26, 2008

(87) PCT Pub. No.: WO2007/113129
PCT Pub. Date: Oct. 11, 2007

(65) Prior Publication Data
US 2010/0174040 A1   Jul. 8, 2010

(30) Foreign Application Priority Data
Mar. 31, 2006   (EP) .................... 06112121

(51) Int. Cl.
*C08F 2/10* (2006.01)
*C08F 4/04* (2006.01)

(52) U.S. Cl. .... 526/219.5; 526/80; 526/210; 526/218.1; 526/227; 526/301; 526/328

(58) Field of Classification Search .......... 526/80, 526/210, 218.1, 219.5, 227, 301, 328
See application file for complete search history.

(56) References Cited

U.S. PATENT DOCUMENTS

| | | |
|---|---|---|
| 3,915,921 A | 10/1975 | Schlatzer, Jr. |
| 4,066,583 A | 1/1978 | Spaulding |
| 4,267,103 A | 5/1981 | Cohen |
| 4,375,533 A | 3/1983 | Park et al. |
| 4,420,596 A | 12/1983 | Lochhead et al. |
| 4,758,641 A | 7/1988 | Hsu |
| 5,306,484 A | 4/1994 | Potthoff-Karl et al. |
| 5,632,976 A | 5/1997 | Chandran et al. |
| 6,262,176 B1 | 7/2001 | Kim et al. |
| 6,277,386 B1 | 8/2001 | Kim et al. |
| 6,319,959 B1 | 11/2001 | Mougin et al. |
| 6,335,003 B1 | 1/2002 | Kim et al. |
| 6,372,876 B1 | 4/2002 | Kim et al. |
| 6,410,004 B1 | 6/2002 | Kim et al. |
| 6,482,393 B1 | 11/2002 | Schehlmann et al. |
| 6,579,517 B1 | 6/2003 | Kim et al. |
| 2003/0113285 A1 | 6/2003 | Meffert et al. |
| 2004/0161387 A1 | 8/2004 | Dupuis et al. |
| 2005/0148753 A1 | 7/2005 | Nguyen-Kim et al. |
| 2005/0169873 A1 | 8/2005 | Rollat et al. |
| 2006/0247403 A1 | 11/2006 | Nguyen-Kim et al. |
| 2007/0141013 A1* | 6/2007 | Nguyen-Kim et al. .... 424/70.15 |
| 2008/0035166 A1 | 2/2008 | Dupuis et al. |
| 2008/0194715 A1 | 8/2008 | Wendel et al. |
| 2008/0199416 A1 | 8/2008 | Nguyen Kim et al. |
| 2008/0227871 A1 | 9/2008 | Kim et al. |
| 2010/0040573 A1 | 2/2010 | Garcia Castro et al. |
| 2010/0068156 A1 | 3/2010 | Kim |

FOREIGN PATENT DOCUMENTS

| | | |
|---|---|---|
| CA | 2382970 | 3/2001 |
| CA | 2574557 | 2/2006 |
| CA | 2591323 | 7/2006 |
| CA | 2615804 A1 | 1/2007 |
| DE | 4223066 | 7/1992 |
| DE | 3750220 T2 | 11/1994 |
| DE | 19943433 | 3/2001 |
| DE | 10259036 | 7/2004 |
| EP | 0037378 | 10/1981 |
| EP | 328725 A2 | 8/1989 |
| EP | 371421 A2 | 6/1990 |
| EP | 0379082 | 7/1990 |
| EP | 584771 A1 | 3/1994 |
| EP | 619111 | 10/1994 |
| EP | 0694565 | 1/1996 |
| EP | 0937451 | 8/1999 |
| EP | 938889 | 9/1999 |
| EP | 957119 | 11/1999 |
| EP | 1035144 A2 | 9/2000 |
| EP | 1435226 A1 | 7/2004 |
| EP | 1543819 | 6/2005 |
| GB | 864311 | 4/1961 |
| WO | WO-80/01164 A1 | 6/1980 |
| WO | WO-9401079 | 1/1994 |
| WO | WO-9403510 | 2/1994 |
| WO | WO-9413724 | 6/1994 |
| WO | WO-9424986 | 11/1994 |
| WO | WO-94024986 | 11/1994 |
| WO | WO-9700664 | 1/1997 |
| WO | WO-9716463 | 5/1997 |
| WO | WO-97/32917 A1 | 9/1997 |
| WO | WO-9958100 | 11/1999 |

(Continued)

OTHER PUBLICATIONS

U.S. Appl. No. 12/299,067, filed Oct. 30, 2008, Kim et al.
U.S. Appl. No. 12/674,581, filed Feb. 22, 2010, Kim et al.
U.S. Appl. No. 12/161,889, filed Jul. 23, 2008, Kim et al.
U.S. Appl. No. 12/865,755, filed Aug. 2, 2010, Kim et al.
U.S. Appl. No. 13/062,197, filed Mar. 3, 2011, Kim et al.

*Primary Examiner* — David W Wu
*Assistant Examiner* — Vu A Nguyen
(74) *Attorney, Agent, or Firm* — Connolly Bove Lodge & Hutz LLP

(57) ABSTRACT

The present invention relates to a method of producing polymers by free-radical polymerization in solution, wherein the polymerization initiator used is an ethanol-soluble initiator, and the solution polymerization is carried out in an alcoholic solvent which comprises 5 to 50% by weight of water.

18 Claims, No Drawings

FOREIGN PATENT DOCUMENTS

| | | |
|---|---|---|
| WO | WO-0110393 | 2/2001 |
| WO | WO-0110394 | 2/2001 |
| WO | WO-0110397 | 2/2001 |
| WO | WO-0116200 | 3/2001 |
| WO | WO-0185821 | 11/2001 |
| WO | WO-03085019 | 10/2003 |
| WO | WO-03091299 | 11/2003 |
| WO | WO-06010571 | 2/2006 |
| WO | WO-06069742 | 7/2006 |
| WO | WO-2006/106114 A1 | 10/2006 |
| WO | WO-2006/106140 A2 | 10/2006 |
| WO | WO-2007/010034 A2 | 1/2007 |
| WO | WO-2007/010035 A1 | 1/2007 |
| WO | WO-2007/012610 A1 | 2/2007 |

* cited by examiner

PROCESS FOR PREPARING ACRYLATE COPOLYMERS

CROSS-REFERENCE TO RELATED APPLICATIONS

This application is a National Stage of PCT/EP2007/052785 filed Mar. 23, 2007 which in turn claims priority from EP Application 06112121.6 filed Mar. 31, 2006, the entire disclosures of which are incorporated herein by reference.

DESCRIPTION

The present invention relates to a method of producing polymers by free-radical polymerization in solution, wherein the polymerization initiator used is an ethanol-soluble initiator, and the solution polymerization is carried out in an alcoholic solvent which comprises 5 to 50% by weight of water.

Numerous methods of producing water-insoluble polymers for hair cosmetics are known from the prior art. These include, for example, solution polymerization, precipitation polymerization, suspension polymerization or emulsion polymerization.

EP-A 0 694 565 describes a method for the homogeneous polymerization of water-insoluble polymers which comprise more than 50% by weight of monomers chosen from the group consisting of C1-C18-alkyl acrylate or methacrylate esters, N-substituted acrylamides or methacrylamides and mixtures thereof, in essentially nonaqueous organic solvents, wherein the polymerization initiator used is a water-soluble initiator which is dissolved in an amount of water sufficient to dissolve the initiator, where the amount of water does not exceed 25% by weight of the total solution and where the polymer obtained is characterized by lower residual monomer contents than are obtained using equivalent amounts of water-insoluble initiators.

It is also described that the use of organic initiators leads to decomposition products with undesired properties such as toxicity and/or bad odor.

WO 94/24986 describes the preparation of hair setting polymers based on acrylic acid and acrylic esters by solution polymerization in ethanol. The polymerization in alcoholic solvents comprising between 4 and 50% by weight of water is not described.

EP-A 0 379 082 describes the preparation of hair-setting polymers based on acrylic acid and acrylic esters by solution polymerization in ethanol. The polymerization in alcoholic solvents comprising between 4 and 50% by weight of water is not described.

The methods known from the prior art often have the disadvantage that the reaction times are long, particularly in the case of polymers comprising acrylic acid, and that the resulting polymers often have high residual monomer contents. To remove the residual monomers, either after polymerization steps and/or complex purification steps are then required.

The polymers obtainable by methods from the prior art often do not have adequately high molecular weights and do not have, for example, the desired flexibility in the hair cosmetic application.

An object of the present invention was therefore to provide an improved method for producing water-insoluble polymers suitable for cosmetic applications which overcomes the disadvantages of the known methods.

This object was achieved by a method of producing polymers which comprise, in copolymerized form, at least 50% by weight of ethylenically unsaturated compounds a) chosen from the group consisting of
ai) $C_1$-$C_{18}$-alkyl (meth)acrylates,
aii) $C_4$-$C_{30}$-alkyl(meth)acrylamides and
aiii) mixtures thereof,
by free-radical polymerization in solution, wherein at least one polymerization initiator is an ethanol-soluble initiator, and the polymerization is carried out in an alcohol-comprising solvent which, based on the solvent, comprises 5 to 50% by weight of water.

For the purposes of the present invention, the expression alkyl comprises straight-chain and branched alkyl groups which, in addition, may also be substituted. Suitable short-chain alkyl groups are straight-chain or branched $C_1$-$C_{18}$-alkyl groups, preferably $C_1$-$C_{12}$-alkyl groups, further preferably $C_1$-$C_8$-alkyl groups and particularly preferably $C_1$-$C_4$-alkyl groups.

These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl etc.

ai) $C_1$-$C_{18}$-alkyl (meth)acrylates

Suitable $C_1$-$C_{18}$-alkyl (meth)acrylates are methyl (meth)acrylate, methyl ethacrylate, ethyl (meth)acrylate, n-propyl (meth)acrylate, i-propyl (meth)acrylate, n-butyl (meth)acrylate, i-butyl (meth)acrylate, sec-butyl (meth)acrylate, tert-butyl (meth)acrylate, 2-pentyl (meth)acrylate, 3-pentyl (meth)acrylate, isopentyl (meth)acrylate, neopentyl (meth)acrylate, n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth)acrylate, nonadecyl (meth)acrylate, arrachinyl (meth)acrylate, behenyl (meth)acrylate, lignocerenyl (meth)acrylate, cerotinyl (meth)acrylate, melissinyl (meth)acrylate, palmitoleinyl (meth)acrylate, oleyl (meth)acrylate, linolyl(meth)acrylate, linolenyl (meth)acrylate, stearyl (meth)acrylate, lauryl (meth)acrylate, phenoxyethyl (meth)acrylate, 4-tert-butyl cyclohexylacrylate, cyclohexyl (meth)acrylate, ureido (meth)acrylate, tetrahydrofurfuryl (meth)acrylate and mixtures thereof.

aii) $C_4$-$C_{30}$-alkyl(meth)acrylamides

Suitable components aii) are (meth)acrylamides which are substituted by $C_4$-$C_{30}$-alkyl radicals, preferably $C_4$-$C_{22}$-alkyl radicals. Preferably, these (meth)acrylamides are chosen from the group consisting of N-n-butyl(meth)acrylamide, N-sec-butyl(meth)acrylamide, N-tert-butyl(meth)acrylamide, N-n-pentyl(meth)acrylamide, N-n-hexyl(meth)acrylamide, N-n-heptyl(meth)acrylamide, i-butyl(meth)acrylamide, tert-butyl(meth)acrylamide, n-octyl(meth)acrylamide, 1,1,3,3-tetramethylbutyl(meth)acrylamide, tert-octyl(meth)acrylamide, ethylhexyl(meth)acrylamide, n-nonyl(meth)acrylamide, n-decyl(meth)acrylamide, n-undecyl(meth)acrylamide, tridecyl(meth)acrylamide, myristyl(meth)acrylamide, pentadecyl(meth)acrylamide, palmityl(meth)acrylamide, heptadecyl(meth)acrylamide, nonadecyl(meth)acrylamide, arrachinyl(meth)acrylamide, behenyl(meth)acrylamide, lignocerenyl(meth)acrylamide, cerotinyl(meth)

acrylamide, melissinyl(meth)acrylamide, palmitoleinyl (meth)acrylamide, oleyl(meth)acrylamide, linolyl(meth)acrylamide, linolenyl(meth)acrylamide, stearyl(meth)acrylamide, lauryl(meth)acrylamide and mixtures thereof.

Preferred components aii) are chosen from the group consisting of isobutyl(meth)acrylamide, tert-butylacrylamide, n-octylacrylamide, 1,1,3,3-tetramethylbutylacrylamide and mixtures thereof.

Suitable N-substituted (meth)acrylamides are also the amides of (meth)acrylic acid with diamines which have one tertiary and one primary or secondary amino group. Of particular suitability are, for example, N-[2-(dimethylamino)ethyl]acrylamide, N-[2-(dimethylamino)ethyl]methacrylamide, N-[3-(dimethylamino)propyl]acrylamide, N[3-(dimethylamino)propyl]methacrylamide, N[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide or N-[4-(dimethylamino)cyclohexyl]methacrylamide and mixtures thereof.

The polymers prepared by the method according to the invention comprise, in copolymerized form, at least 50% by weight, preferably at least 55% by weight, particularly preferably at least 60% by weight and in particular at least 70% by weight, of compounds chosen from the group consisting of $C_1$-$C_{18}$-alkyl (meth)acrylates, (meth)acrylamides and mixtures thereof.

The polymers produced by the method according to the invention comprise at most 95% by weight, preferably at most 90% by weight, particularly preferably at most 80% by weight and in particular at most 75% by weight, of compounds chosen from the group consisting of $C_1$-$C_{18}$-alkyl (meth)acrylates, (meth)acrylamides and mixtures thereof.

Further Monomers b)

The polymers obtainable by the method according to the invention preferably also comprise further monomers b) in copolymerized form. These may be all free-radically polymerizable compounds which can be polymerized to give cosmetically acceptable copolymers.

Such preferred further monomers are:

bi) anionic or anionogenic, free-radically polymerizable compounds an anionogenic compound is understood as meaning a compound which can be converted into the corresponding anionic form by deprotonation with bases. Preferably, the anionic or anionogenic compounds are chosen from the group consisting of (meth)acrylic acid, ethacrylic acid, α-chloroacrylic acid, crotonic acid, maleic acid, maleic anhydride, itaconic acid, citraconic acid, mesaconic acid, glutaconic acid, aconitic acid, fumaric acid and mixtures thereof, where (meth)acrylic acid and, in particular, methacrylic acid and mixtures of anionic or anionogenic compounds comprising methacrylic acid. Further suitable are also half-esters of monoethylenically unsaturated dicarboxylic acids having 4 to 10, preferably 4 to 6, carbon atoms, e.g. of maleic acid, such as monomethyl maleate.

Particularly preferred anionic or anionogenic compounds are acrylic acid, methacrylic acid, itaconic acid and mixtures thereof.

In one preferred embodiment, the weight ratio of methacrylic acid used for the polymerization to these further compounds, such as, for example, acrylic acid, is preferably at least 2:1, particularly preferably at least 2.5:1 and in particular at least 3:1, where the quantitative data refers to the acid form of the compounds bi).

Anionic or anionogenic compounds are also the salts of the abovementioned acids. These include all salts which can be obtained by reacting the acids with bases. These are, in particular, the sodium, potassium, ammonium salts and the salts from the reaction of the acids with cosmetically customary bases carrying OH groups, such as triethanolamine or 2-amino-2-methylpropanol (AMP).

bii) esters of α,β-ethylenically unsaturated mono- and dicarboxylic acids with $C_2$- to $C_{12}$-amino alcohols which are $C_1$-$C_8$-dialkylated on the amine nitrogen.

Suitable compounds of this type are, for example, N,N-dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminocyclohexyl (meth)acrylate etc. Preference is given to N,N-dimethylaminopropyl acrylate and N,N-dimethylaminopropyl (meth)acrylate;

biii) esters of α,β-ethylenically unsaturated mono- and dicarboxylic acids with polyhydric alcohols, in particular diols.

Preferred compounds of this type are esters of acrylic acid, methacrylic acid or ethacrylic acid with diols, such as, for example, 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate, neopentyl glycol mono(meth)acrylate, 1,5-pentanediol mono(meth)acrylate, 1,6-hexanediol mono(meth)acrylate and mixtures thereof.

biv) amides of α,β-ethylenically unsaturated mono- and dicarboxylic acids with diamines which have at least one primary or secondary amino group. Preference is given to diamines which have one tertiary and one primary or secondary amino group. Preferably, the monomers e) used are N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N[2-(diethylamino)ethyl]acrylamide, N-[4-(dimethylamino)cyclohexyl]acrylamide and N-[4-(dimethylamino)cyclohexyl]methacrylamide. Particular preference is given to using N-[3-(dimethylamino)propyl]acrylamide and/or N-[3-(dimethylamino)propyl]methacrylamide.

bv) vinyl- and allyl-substituted heteroaromatic compounds

Suitable compounds of this type are, for example, 2- and 4-vinylpyridine, allylpyridine, and preferably N-vinyl heteroaromatics, such as N-vinylimidazole or N-vinyl-2-methylimidazole; N-vinylimidazoles of the general formula VII, in which $R^1$ to $R^3$ is hydrogen, $C_1$-$C_4$-alkyl or phenyl

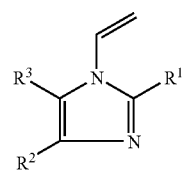

(VII)

Examples of compounds of the general formula VII are given in table 1 below:

TABLE 1

| $R^1$: | $R^2$: | $R^3$: |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl;
Ph = phenyl bvi) essentially hydrophilic, nonionic compounds

Preferred compounds of this type are N-vinylamides, N-vinyllactams, vinyl- and allyl-substituted heteroaromatic compounds, polyether acrylates; preferred N-vinyl-lactams are, for example, those which have one or more $C_1$-$C_6$-alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam and N-vinyl-7-ethyl-2-caprolactam, where N-vinylpyrrolidone and N-vinylcaprolactam are particularly preferred.

bvii) olefinically unsaturated free-radically polymerizable compounds containing urethane groups The component bvii) used is advantageously at least one olefinically unsaturated compound containing urethane groups. For the purposes of the present invention, olefinically unsaturated compounds containing urethane groups are understood as meaning compounds which comprise at least one urethane group and at least one free-radically polymerizable olefinic double bond.

Olefinically unsaturated prepolymers comprising urethane groups and suitable as component bvii) for the polymers obtainable by the method according to the invention are specified, for example, in P.K.T. Oldring (Ed.), Chemistry and Technology of UV- and EB-Formulations for Coatings, Inks and Paints, Vol. 11, SITA Technology, London, 1991, pp. 73-123, to the entire contents of which reference is hereby made. (Poly)urethane (meth)acrylates are known to the person skilled in the art. They can be obtained by reacting a di- or polyisocyanate with a chain extender from the group of diols/polyols and/or diamines/polyamines and/or dithiols/polythiols and/or alkanolamines and subsequent reaction of the remaining free isocyanate groups with at least one hydroxyalkyl (meth)acrylate or hydroxyalkyl esters of other ethylenically unsaturated carboxylic acids. The amounts of chain extenders, di- or polyisocyanate and hydroxyalkyl esters are preferably chosen here so that
1.) the equivalent ratio of the NCO groups to the reactive groups of the chain extender (hydroxyl, amino or mercaptyl groups) is between 3:1 and 1:2, preferably about 2:1 and
2.) the OH groups of the hydroxyalkyl esters of the ethylenically unsaturated carboxylic acids are present in stoichiometric amounts in relation to the still free isocyanate groups of the prepolymer of isocyanate and chain extender.

It is also possible to produce (poly)urethane (meth)acrylates by firstly reacting some of the isocyanate groups of a di- or polyisocyanate with at least one hydroalkyl ester, and then reacting the remaining isocyanate groups with a chain extender. In this case, too, the amounts of chain extender, isocyanate and hydroxyalkyl ester are chosen so that the equivalent ratio of the NCO groups to the reactive groups of the chain extender is between 3:1 and 1:2, preferably about 2:1, and the equivalent ratio of the remaining NCO groups to the OH groups of the hydroxyalkyl ester is about 1:1. All intermediate forms of these two methods are of course also possible. For example, some of the isocyanate groups of a diisocyanate can firstly be reacted with a diol, then more of the isocyanate groups can be reacted with the hydroxyalkyl ester and, subsequently to this, the remaining isocyanate groups can be reacted with a diamine. The various preparation methods of the polyurethane (meth)acrylates are known (e.g. from EP-A 0 203 161) and therefore require no detailed description.

Urethane (meth)acrylates suitable as component bvii) are also described in DE-A 198 38 852 p. 3, l.45 to p. 9, l.20, to the entire contents of which reference is made at this point.

Urethane (meth)acrylates are also understood as meaning compounds which comprise, in incorporated form,
A) at least one compound which comprises at least one active hydrogen atom and at least one free-radically polymerizable, α,β-ethylenically unsaturated double bond per molecule,
B) at least one diisocyanate and
C) at least one compound which comprises two active hydrogen atoms per molecule,
and the salts thereof.

Component A)

Suitable compounds A) are, for example, the customary vinyl compounds known to the person skilled in the art which additionally have at least one group reactive toward isocyanate groups, which is preferably chosen from hydroxyl groups and primary and secondary amino groups. These include, for example, the esters of α,β-ethylenically unsaturated mono- and dicarboxylic acids with at least dihydric alcohols.

The α,β-ethylenically unsaturated mono- and/or dicarboxylic acids used may, for example, be acrylic acid, methacrylic acid, fumaric acid, maleic acid, crotonic acid, itaconic acid etc. and mixtures thereof.

Suitable alcohols are customary diols, triols and polyols, e.g. 1,2-ethanediol, 1,3-propanediol, 1,4-butanediol, 1,5-pentanediol, 1,6-hexanediol, 1,10-decanediol, diethylene glycol, 2,2,4-trimethylpentanediol-1,5,2,2-dimethylpropanediol-1,3, 1,4-dimethylolcyclohexane, 1,6-dimethylolcyclohexane, glycerol, trimethylolpropane, erythritol, pentaerythritol and sorbitol.

The compounds A) are, for example, hydroxymethyl (meth)acrylate, hydroxyethyl ethacrylate, 2-hydroxyethyl (meth)acrylate, 2-hydroxypropyl (meth)acrylate, 3-hydroxypropyl (meth)acrylate, 3-hydroxybutyl (meth)acrylate, 4-hydroxybutyl (meth)acrylate, 6-hydroxyhexyl (meth)acrylate, 3-hydroxy-2-ethylhexyl (meth)acrylate, and di(meth)acrylic esters of 1,1,1-trimethylolpropane or of glycerol.

Suitable compounds A) are also the esters and amides of the above-mentioned α,β-ethylenically unsaturated mono- and dicarboxylic acids with $C_2$- to $C_{12}$-amino alcohols which have a primary or secondary amino group. These include aminoalkyl acrylates and aminoalkyl methacrylates and N-monoalkyl derivates thereof which carry, for example, an N—$C_1$- to $C_8$-monoalkyl radical, such as aminomethyl (meth)acrylate, aminoethyl (meth)acrylate, N-methylaminomethyl (meth)acrylate, N-ethylaminomethyl (meth)acrylate, N-ethylaminoethyl (meth)acrylate, N-(n-propyl)aminomethyl (meth)acrylate, N-isopropylaminomethyl (meth) acrylate and preferably tert-butylaminoethyl acrylate and tert-butylaminoethyl methacrylate. These also include N-(hydroxy-$C_1$- to $C_{12}$-alkyl)(meth)acrylamides, such as N-hydroxymethyl(meth)acrylamide, N-hydroxyethyl(meth)acrylamide etc.

Suitable compounds A) are also the amides of the abovementioned α,β-ethylenically unsaturated mono- and dicarboxylic acids with di- and polyamines which have at least two primary or two secondary or one primary and one secondary amino group(s). These include, for example, the corresponding amides of acrylic acid and methacrylic acid, such as aminomethyl(meth)acrylamide, aminoethyl(meth)acrylamide, aminopropyl(meth)acrylamide, amino-n-butyl(meth)acrylamide, methylaminoethyl(meth)acrylamide, ethylaminoethyl(meth)acrylamide, methylaminopropyl(meth)acrylamide, ethylaminopropyl(meth)acrylamide or methylamino-n-butyl(meth)acrylamide.

Suitable compounds A) are also the reaction products of epoxide compounds which have at least one epoxide group with the abovementioned α,β-ethylenically unsaturated mono- and/or dicarboxylic acids and anhydrides thereof. Suitable epoxide compounds are, for example, glycidyl ethers, such as bisphenol-A-diglycidyl ether, resorcinol diglycidyl ether, 1,3-propanediol diglycidyl ether, 1,4-butanediol diglycidyl ether, 1,5-pentanediol diglycidyl ether or 1,6-hexanediol diglycidyl ether.

Component B)

Component B) is customary aliphatic, cycloaliphatic and/or aromatic diisocyanates, such as tetramethylene diisocyanate, hexamethylene diisocyanate, methylenediphenyl diisocyanate, 2,4- and 2,6-tolylene diisocyanate and isomer mixtures thereof, o- and m-xylylene diisocyanate, 1,5-naphthylene diisocyanate, 1,4-cyclohexylene diisocyanate, dicyclohexylmethane diisocyanate and mixtures thereof. Preferably, component B) is hexamethylene diisocyanate, isophorone diisocyanate, o- and m-xylylene diisocyanate, dicyclohexylmethane diisocyanate and mixtures thereof. If desired. up to 3 mol % of said compounds can be replaced by triisocyanates.

Component C)

Suitable compounds C) are, for example, diols, diamines, amino alcohols and mixtures thereof. If desired, up to 3 mol % of said compounds can be replaced by triols or triamines.

Suitable diols C) are, for example, ethylene glycol, propylene glycol, butylene glycol, neopentyl glycol, cyclohexanedimethylol, di-, tri-, tetra-, penta- or hexaethylene glycol and mixtures thereof. Preference is given to using neopentyl glycol and/or cyclohexanedimethylol.

Suitable amino alcohols C) are, for example, 2-aminoethanol, 2-(N-methylamino)ethanol, 3-aminopropanol, 4-aminobutanol, 1-ethylaminobutan-2-ol, 2-amino-2-methyl-1-propanol or 4-methyl-4-aminopentan-2-ol.

Suitable diamines C) are, for example, ethylenediamine, propylenediamine, 1,4-diaminobutane, 1,5-diaminopentane and 1,6-diaminohexane.

Preferred compounds C) are polymers with a number-average molecular weight in the range from about 300 to 5000, preferably about 40 to 4000, in particular 500 to 3000. These include, for example, polyesterdiols, polyetherols, α,ω-diaminopolyethers and mixtures thereof. Preferably, polymers containing ether groups are used.

The polyetherols C) are preferably polyalkylene glycols, e.g. polyethylene glycols, polypropylene glycols, polytetrahydrofurans etc., block copolymers of ethylene oxide and propylene oxide or block copolymers of ethylene oxide, propylene oxide and butylene oxide which comprise the copolymerized alkylene oxide units in random distribution or in the form of blocks.

Suitable α,ω-diaminopolyethers C) can be prepared, for example, by amination of polyalkylene oxides with ammonia.

Suitable polytetrahydrofurans C) can be prepared by cationic polymerization of tetrahydrofuran in the presence of acidic catalysts, such as, for example, sulfuric acid or fluorosulfuric acid. Such preparation processes are known to the person skilled in the art.

Suitable polyesterdiols C) preferably have a number-average molecular weight in the range from about 400 to 5000, preferably 500 to 3000, in particular 600 to 2000.

Suitable polyesterdiols are all those which are usually used for the preparation of polyurethanes, in particular those based on aromatic dicarboxylic acids, such as terephthalic acid, isophthalic acid, phthalic acid, Na or K sulfoisophthalic acid etc., aliphatic dicarboxylic acids, such as adipic acid or succinic acid etc., and cycloaliphatic dicarboxylic acids, such as 1,2-, 1,3- or 1,4-cyclohexanedicarboxylic acid.

Suitable diols are, in particular, aliphatic diols, such as ethylene glycol, propylene glycol, 1,6-hexanediol, neopentyl glycol, diethylene glycol, polyethylene glycols, polypropylene glycols, 1,4-dimethylolcyclohexane, and poly(meth) acrylate diols of the formula

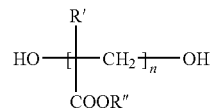

in which R' is H or $CH_3$ and R" is $C_1$-$C_{18}$-alkyl (in particular $C_1$-$C_{12}$— or $C_1$-$C_8$-alkyl) which have a molar mass of up to about 3000. Diols of this type can be prepared in the usual manner and are commercially available (Tegomer grades MD, BD and OD from Goldschmidt).

Preference is given to polyesterdiols based on aromatic and aliphatic dicarboxylic acids and aliphatic diols, in particular those in which the aromatic dicarboxylic acid constitutes 10 to 95 mol %, in particular 40 to 90 mol % and preferably 50 to 85 mol %, of the total dicarboxylic acid fraction (remainder aliphatic dicarboxylic acids).

Particularly preferred polyesterdiols are the reaction products of phthalic acid/diethylene glycol, isophthalic acid/1,4-butanediol, isophthalic acid/adipic acid/1,6-hexanediol, 5-$NaSO_3$-isophthalic acid/phthalic acid/adipic acid/1,6-hexanediol, adipic acid/ethylene glycol, isophthalic acid/adipic acid/neopentyl glycol, isophthalic acid/adipic acid/neopentyl glycol/diethylene glycol/dimethylolcyclohexane and 5-$NaSO_3$-isophthalic acid/isophthalic acid/adipic acid/neopentyl glycol/diethylene glycol/dimethylocyclohexane.

The compounds C) can be used individually or as mixtures. Further suitable urethane (meth)acrylates are given in DE-A 198 38 852 p. 5, l.40 to p. 9, l.20, to the entire contents of which reference is hereby made. Of particular suitability are the urethanediacrylates described in DE-A 198 38 852, table 1.

As suitable components bvii), mention may further be made of:
bviia) reaction products of the reaction of hydroxy (meth) acrylates with diols and/or OH-terminated polyols and/or OH-terminated polyesters and/or diamines and diisocyanates. Such difunctional urethane acrylate oligomers and their preparation are described, for example, in WO 97/00664, p. 5, l.17 to p. 6, l.8 and the corresponding examples, to which reference is hereby made in their entirety.

bviib) carbamoyloxycarboxylates of the general formula I

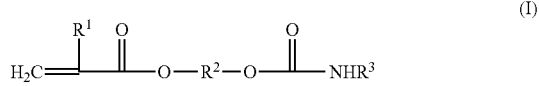

where
R¹ is H, halogen or C1-C8-alkyl,
R² is optionally substituted $C_1$-$C_{12}$-alkylene, -arylene, -alkylarylene or -arylalkylene, polyoxyalkylene,
R³ is $C_1$-$C_6$-alkyl.

Such carbamoyloxycarboxylates of the general formula I are disclosed in U.S. Pat. Nos. 3,479,328 and 3,674,838, to the entire contents of which reference is hereby made.

bviic) the divinylurethanes of the general formula II disclosed in GB 1 443 715

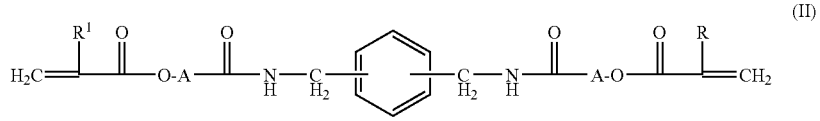

where
R is H or methyl
A is (poly)alkyleneoxy
and vinylurethanes of the general formula III

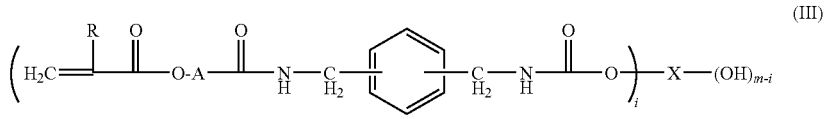

where R and A are as defined in formula II, and X and n are as defined in GB 1 443 715 p. 2, l.9-13. The vinylurethanes, likewise described in GB 1 443 715, to the entire contents of which reference is hereby made, are further possible components c) of the polymers which can be prepared by the method according to the invention.

bviid) the N-substituted carbamoyloxyalkyleneoxyalkyl (meth)acrylates of the general formula IV and described in EP-A 0 036 813, to the entire contents of which reference is hereby made,

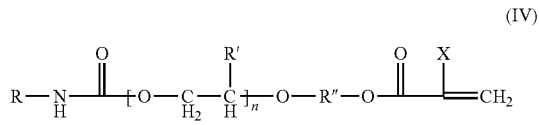

where R, R', R" and X are as defined in EP-A 0 036 813, p. 2, l.13-28, and n is an integer from 0 to 20, preferably from 1 to 6 and particularly preferably from 1 to 4.

bviie) the urethane acrylate compounds known from DE-A-4 007 146, to the entire contents of which reference is hereby made, which are obtainable by reacting polyisocyanates with hydroxyalkyl acrylates, followed by a reaction with primary or secondary amines.

bviif) products of the reaction of isocyanates with polyols and hydroxyalkyl acrylates as described, for example, in DE 27 26 041 A, U.S. Pat. No. 4,260,703 and U.S. Pat. No. 4,481,093, and products of the reaction of isocyanates with hydroxyalkyl acrylates as described in JP 63297369 and JP 59157112, to the entire contents of which reference is hereby made.

bviig) the prepolymers comprising urethane groups described in EP-A 0 903 363, to the entire contents of which reference is hereby made, which can be prepared by a method where a component A comprising isocyanate groups is reacted with a component B comprising OH groups, where component A comprises at least one trifunctional isocyanate compound A1 and if appropriate one or more difunctional isocyanate compounds A2, and the component B comprising OH groups comprises at least one olefinically unsaturated compound B1 with at least one reactive OH group and, if appropriate, compounds B2 comprising OH groups different therefrom, where either the component A comprises two different isocyanate compounds A1 or one isocyanate compound A1 and at least one isocyanate compound A2, or the component B comprises at least two different compounds B2.

bviih) polyurethane polymers which A) 40 to 80% by weight, based on the total weight of components A) to F), of at least one prepolymer containing hydroxyl groups with at least one free-radically or photochemically polymerizable α,β-ethylenically unsaturated double bond, where the prepolymer A) is a reaction product or a mixture of a) at least one polyester acrylate and/or polyether acrylate and/or polyurethane acrylate and b) at least one epoxy acrylate, B) comprises 0.1 to 20% by weight, based on the total weight of components A) to F), of at least one compound with at least one hydroxyl and/or primary or secondary amino group reactive toward isocyanate groups and additionally at least one polar functional group, C) 0.1 to 10% by weight, based on the total weight of components A) to F), of at least one compound chosen from diamines, polyamines and mixtures thereof, D) 0 to 20% by weight, based on the total weight of components A) to F), of at least one further compound different from A), B), C) and E) with at least two groups reactive toward isocyanate groups, which are hydroxyl groups and mixtures of hydroxyl groups and/or primary or secondary amino groups, E) 0 to 20% by weight, based on the total weight of components A) to F), of at least one compound with a group reactive toward isocyanate groups, F) 10 to 50% by weight, based on the total weight of components A) to F), of at least one polyisocyanate in copolymerized form, and the salts thereof, wherein the sum of the hydroxyl numbers of components A) and D) is in a range from 121 to 300 mg of KOH/g.

These polyurethane polymers are described in EP-A 0 942 022, to the entire contents of which reference is hereby made.

bviij) the reaction products described in EP-A 1 002 818 (to the entire contents of which reference is hereby made) of
a) isocyanate trimer (mixtures) based on aliphatic or cycloaliphatic diisocyanates which consist of up to 100 mol % of compounds of the iminooxadiazinedione structure type of the formula A,

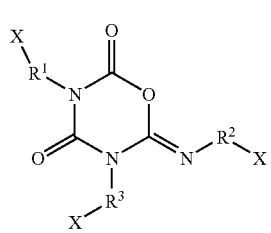

(A)

in which $R^1$, $R^2$ and $R^3$, independently of one another, are if appropriate branched C4-C20-(cyclo)alkylene, and X is identical or different radicals of isocyanate or of isocyanate secondary products which are of the iminooxadiazinedione, isocyanurate, uretdione, urethane, allophanate, biuret or oxadiazinetrione structure type and carry the above-mentioned radicals $R^1$, $R^2$ and $R^3$ in the N position, with b) an alcohol component which comprises at least one monovalent hydroxy-functional if appropriate branched $C_1$-$C_{12}$-alkyl ester of (meth)acrylic acid.

bviik) the polyurethanes comprising allyl groups and of the general formula V, as disclosed in WO 01/72862, to the entire contents of which reference is hereby made:

$$R^1\text{—[NHCO(OR)}_y\text{(OCH}_2\text{CH=CH}_2)_m]_n \qquad (V)$$

The meanings of R, $R^1$, y, m and n are described in WO 01/72862 on p. 3, l.29 to p. 4, l.10.

bviil) the (meth)acrylic esters containing urethane groups described in WO 04/050888, to the entire contents of which reference is hereby made, which can be prepared by reacting an alcohol containing urethane groups with (meth)acrylic acid or an ester of (meth)acrylic acid with a saturated alcohol and if appropriate purification of the reaction mixture, the reaction being carried out in the presence of an enzyme (E).

bviim) the urethane (meth)acrylate oligomers described in WO 98/06783, to the entire contents of which reference is made at this point, in particular to p. 1, l.22 to p. 2, l.6.

bviin) the polyurethanes described in DE 44 34 554 A1, to the entire contents of which reference is made at this point, in particular to p. 2, l.42 to p. 4, l.27.

bviio) the urethane (meth)acrylate oligomers described in WO 04/067599, to the entire contents of which reference is hereby made, in particular to p. 10, l.24 to p. 12, l.13.

bviip) the urethane acrylates described in U.S. Pat. No. 5,240,835, to the entire contents of which reference is made at this point, which can be prepared by transesterifying alkyl acrylates with alcohols with catalysis of a biocatalyst from *Corynebacterium oxydans*.

bviiq) the carbamoyloxy(meth)acrylates described in WO 04/052843, to the entire contents of which reference is hereby made at this point, which can be prepared by a method as described on p. 3, l.34 to p. 10, l.28 of WO 04/052843.

bviir) the carbamoyloxy(meth)acrylates which are described in WO 94/25537 p. 8, l.29 to p. 9, l.32, to the entire contents of which reference is made at this point.

bviis) the polyisocyanate secondary products described in DE-A 102 46 112, to the entire contents of which reference is hereby made, comprising at least one allophanate group which carries, on the oxygen atom of the allophanate group bonded via two single bonds, at least one acrylate, methacrylate or vinyl ether double bond, wherein a polyisocyanate or polyisocyanate secondary product comprising at least one oxadiazinetrione group reacts with an alcohol comprising acrylate, methacrylate or vinyl ether double bond at temperatures between −20 and 100° C.

bviit) WO 00/39183, to the entire contents of which reference is hereby made, describes compounds with isocyanate groups or capped isocyanate groups, allophanate groups and free-radically polymerizable C—C double bonds, where the C—C double bonds are activated by a carbonyl group bonded directly thereto or an O atom in ether function (activated double bonds), derived from polyisocyanates and alcohols A which, besides the alcohol group, also carry an activated double bond.

These compounds are preferably reacted with alcohols ROH which only carry one OH group or with amines $RNH_2$ or RR'NH in at least the amount which suffices to convert all isocyanate groups and capped isocyanate groups into urethane or urea groups. Here, R and R', independently of one another, are $C_1$-$C_{12}$-alkyl, -aryl, -alkylaryl or -arylalkyl, polyoxyalkylene, where the radicals may, if appropriate, be functionalized with hydroxyl groups.

Preferred alcohols for this reaction are $C_1$-$C_{12}$—, in particular $C_1$-$C_4$-alkanols, such as, for example, methanol, ethanol, n-propanol, isopropanol, n-butanol, isobutanol, sec-butanol, tert-butanol.

Preferred amines for this reaction are $C_1$-$C_{12}$—, in particular $C_1$-$C_4$-(di)alkylamines, (di)alkanolamines, alkylalkanolamines, such as, for example, ethylamine, butylamine, diethylamine, ethanolamine, diethanolamine, 2-amino-2-methylpropanol.

In this way, for example, compounds of the following general formulae are obtained: from the reaction with alcohols:

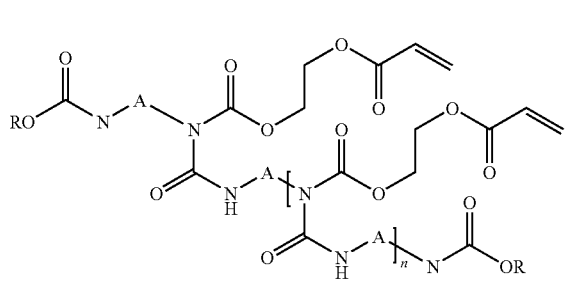

from the reaction with amines:

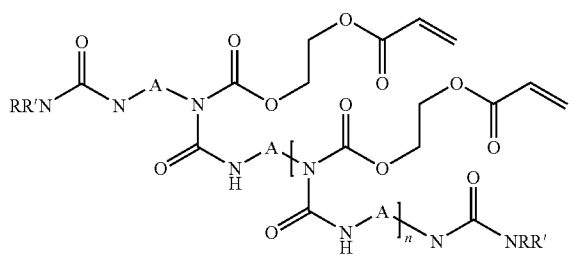

where
R is $C_1$-$C_{12}$-alkyl, -aryl, -alkylaryl or -arylalkyl, polyoxyalkylene, if appropriate functionalized with hydroxyl groups
R' is H, $C_1$-$C_{12}$-alkyl, -aryl, -alkylaryl or -arylalkyl, polyoxyalkylene, if appropriate functionalized with hydroxyl groups
n is 0 to 10, preferably 0 to 5, particularly preferably 0 to 2
A is $C_1$-$C_{12}$-alkylene, -arylene, -alkylarylene or -arylalkylene, polyoxyalkylene and mixtures thereof.

The corresponding methacrylate derivatives of these compounds can of course also be used as component c).

Suitable components c) are, for example, also
bviiu) N-butyl-2-hydroxyethylcarbamates (CAS 63225-53-6) of the formula

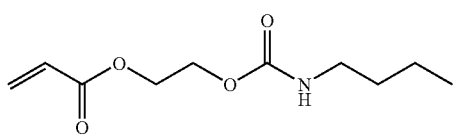

(as commercially available, for example, as Ebecryl®CL 1039 (UCB)) and the corresponding methacrylic acid derivative,
bviiv) N-methyl-2-hydroxyethylcarbamates (CAS 52607-81-5) of the formula

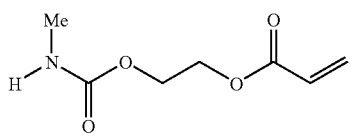

and the corresponding methacrylic acid derivative,
bviiw) one of or a mixture of the two components of the following formulae (the mixture is referred to herein as monomer C22 (see also the examples)):

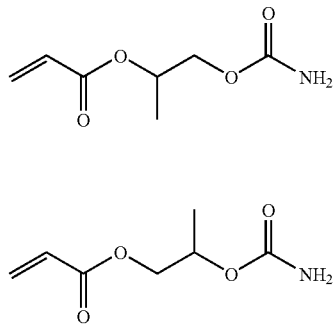

and the corresponding methacrylic acid derivatives,
bviix) one of or a mixture of the two components of the following formulae

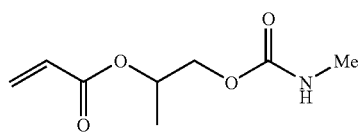

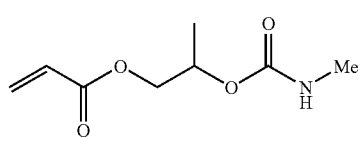

and the corresponding methacrylic acid derivatives,
bviiy) compound of the following formula

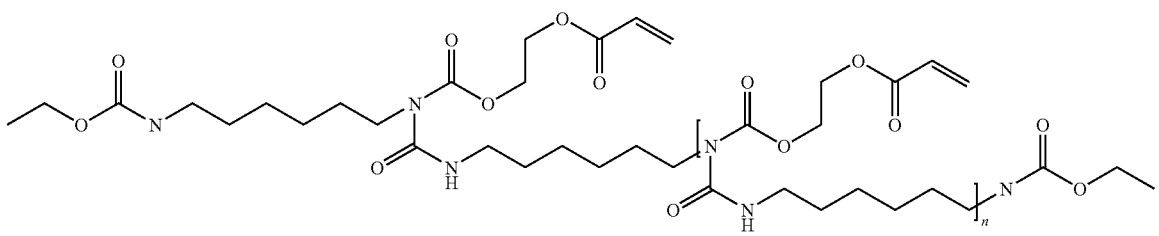

where n is 0 to 10, preferably 0 to 4, particularly preferably 0 to 2,
and the corresponding methacrylic acid derivatives.
bviiz) diurethane dimethacrylate 7,7,9-(or 7,9,9-)trimethyl-4,13-dioxo-3,14-dioxa-5,12-diaza-hexadecane-1,16-diol dimethacrylate (CAS 72869-86-4), which is commercially available, for example, as PLEX®6661-O (Degussa).

Polyurethane (meth)acrylates suitable as component bvii), such as polyurethane mono-, di-, tri-, tetra-, penta- or hexa-(meth)acrylates, are commercially available under the brands Laromer® (BASF), Photomer® (Cognis), Sartomer® (Sartomer) or Ebecryl® (UCB).

They can also be used in pure form (without diluents), as solutions in solvents such as ethanol or butyl acetate, or as solutions in reactive diluents (such as, for example, tripropylene glycol diacrylate (TPGDA), hexanediol diacrylate (HDDA), dipropylene glycol diacrylate (DPGDA), trimethylolpropane formal monoacrylate (Laromer®LR 8887), trimethylolpropane triacrylate (TMPTA), propoxylated glycerol triacrylate (GPTA), ethoxylated trimethylolpropane triacrylate (EO3TMPTA), ethoxyethoxyethyl acrylate (EOEOEA), PEG 400 diacrylate (PEG400DA), isobornyl acrylate (IBOA), propoxylated neopentyl glycol diacrylate (PO2NPGDA), 2-phenoxyethyl acrylate (POEA), butanediol diacrylate (BDDA), butanediol acrylate (BDMA), dihydrodicyclopentadienyl acrylate (DCPA), triethylene glycol divinyl ether, ethyl digycol acrylate (EDGA), lauryl acrylate (LA), 4-t-butylcyclohexyl acrylate (TBCH), or as aqueous emulsions.

Such polyurethane (meth)acrylates are:

Laromer® grades LR 8949, LR 9005, LR 8983, UA 19 T, UA 9030V, UA 9028V, UA 9029V, UA 9033V, UA 9031V and LR 8987, Photomer® grades 6891, 6892, 6893-20R, 6572, 6010, 6019, 6184, 6210, 6217, 6230, 6363 and 6008

Sartomer® CN grades, such as, for example, the aliphatic urethane acrylates CN 934 CN 934X50, CN 944B85, CN 945A60, CN 945B85, CN 953B70, CN 961E75, CN 961H81, CN 962, CN 963A80, CN 963B80, CN 963E75, CN 963E80, CN 963J85, CN 964, CN 964A85, CN 964B85, CN 964H90, CN 964E75, CN 965, CN 965A80, CN 966A80, CN 966B85, CN 966H90, CN 966I80, CN 966J75, CN 966R60, CN 968, CN 982E75, CN 982P90, CN 983, CN 983B88, CN 984, CN 985B88 and the aromatic urethane acrylates CN 970A60, CN 970E60, CN 970H75, CN 971A80, CN 972, CN 973A80, CN 973H85, CN 973J75, CN 975, CN 977C70, CN 978, CN 980, CN 980M50, CN 981, CN 981A75, CN 981B88, CN 982A75, CN 982B88

Ebecryl® grades, such as, for example, 220, 230, 244, 264, 265, 270.

As compound bvii), particular preference is given to carbamoyloxycarboxylates of the general formula VIII

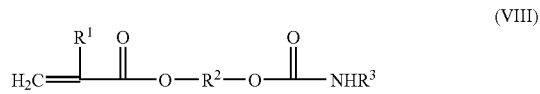

where $R^1$ is H, halogen, $C_1$-$C_8$-alkyl, preferably H or methyl, $R^2$ is optionally substituted $C_1$-$C_{12}$-alkylene, -arylene, -alkylarylene or -arylalkylene, optionally hydroxy-substituted polyoxyalkylene, $R^3$ is H, $C_1$-$C_8$-alkyl.

In general, preference is given to those compounds bvii) which comprise at most 4, preferably at most 3 and particularly preferably at most 2, free-radically polymerizable double bonds per molecule.

The polymers obtainable by the method according to the invention comprise 0-30% by weight, preferably 0.1-20% by weight, particularly preferably 0.5-10% by weight and most preferably 0.5-5% by weight, of the compound iii) in copolymerized form.

bviii) essentially hydrophobic, nonionic compounds preferably, compounds of this type are, for example, the esters of vinyl alcohol or allyl alcohol with $C_1$-$C_{30}$-monocarboxylic acids, vinyl ethers, vinylaromatics, vinyl halides, vinylidene halides, $C_2$-$C_8$-monoolefins, nonaromatic hydrocarbons with at least 2 conjugated double bonds and mixtures thereof; suitable examples are vinyl formiate, vinyl acetate, vinyl propionate, vinyl-n-butyrate, vinyl stearate, vinyl laurate, styrene, α-methylstyrene, o-chlorostyrene, acrylonitrile, methacrylonitrile, vinyltoluenes, vinyl chloride, vinylidene chloride, vinyl fluoride, vinylidene fluoride, ethylene, propylene, isobutene, butadiene, isoprene, chloroprene, methyl, ethyl, butyl, dodecyl vinyl ethers and mixtures thereof.

bix) Polyesters with at least two free-radically polymerizable, olefinically unsaturated double bonds The term polyester is known to the person skilled in the art. Polyesters are polymers with ester bonds —[—CO—O—]— in the main chain. Components bix) according to this invention are, for example, polyester (meth)acrylates which comprise at least two free-radically polymerizable, olefinally unsaturated double bonds per molecule. Polyester (meth)acrylates are known in principle to the person skilled in the art. They can be prepared by various methods. For example, (meth)acrylic acid can be used directly as acid component when constructing the polyesters. In addition, it is possible to use hydroxyalkyl esters of (meth)acrylic acid as alcohol component directly for constructing the polyesters. Preferably, the polyester (meth)acrylates, however, are prepared by (meth)acrylation of polyesters. For example, polyesters containing hydroxyl groups can firstly be constructed, which are then reacted with acrylic acid or methacrylic acid. Preferably, at least two of the hydroxyl groups per molecule of the polyester containing hydroxyl groups are reacted with (meth) acrylic acid, so that, per molecule of the reaction product, at least two free-radically polymerizable, olefinally unsaturated double bonds are present.

It is also possible to firstly construct polyesters containing carboxyl groups, which are then reacted with a hydroxyalkyl ester of acrylic or methacrylic acid. Here too, at least two of the carboxyl groups per molecule of the polyester containing carboxyl groups are reacted with the hydroxyalkyl ester of (meth)acrylic acid, meaning that, per molecule of the reaction product, at least two free-radically polymerizable, olefinally unsaturated double bonds are present. It is preferred to use mixtures of polyester (meth)acrylates which comprise, on average, more than two free-radically polymerizable, olefinally unsaturated double bonds per molecule of polyester (meth)acrylate.

Polyester acrylates suitable as component bix) are described, for example, in EP-A 0 279 303, to which reference is made here in its entirety (EP-A 0 279 303, p. 5, l.28-44).

DE 2 853 921 also describes suitable polyester acrylates, namely those of aliphatic and/or aromatic dicarboxylic acids, such as succinic acid, glutaric acid, adipic acid, pimelic acid, suberic acid, azelaic acid, sebacic acid, cyclohexanedicarboxylic acid, phthalic acid, isophthalic acid, terephthalic acid, maleic acid, fumaric acid, itaconic acid and derivatives thereof and polyhydric alcohols, such as ethylene glycol, polyethylene glycols, propylene glycol, polypropylene glycols, butanediol, hexanediol, neopentyl glycol, hydroxypivalic neopentyl glycol ester, trimethylolpropane, glycerol, pentaerythritol and/or trishydroxyethyl isocyanurate, and α,β-ethylenically unsaturated monocarboxylic acids, for example acrylic acid, methacrylic acid, crotonic acid, cinnamic acid and/or dicarboxylic half-esters of monoalkanols, such as maleic, fumaric and itaconic half-esters with $C_1$-$C_4$-monoalcohols, with acrylic acid and methacrylic acid being preferred.

EP-A 0 686 621, to which reference is made here in its entirety, also describes suitable components bix). These are reaction products of (meth)acrylic acid with a hydroxy compound. Suitable hydroxy compounds are compounds with one or more hydroxy groups.

Monoalcohols, $C_2$-$C_6$-alkylenediols, trimethylolpropane, glycerol or pentaerythritol or, for example, compounds comprising hydroxy groups and alkoxylated with ethylene oxide or propylene oxide are mentioned.

In addition, suitable hydroxy compounds are polyesters containing hydroxyl groups. Such polyesters containing hydroxyl groups can be produced, for example, in the usual manner by esterification of dicarboxylic acids or polycarboxylic acids with diols or polyols. The starting substances for such polyesters containing hydroxyl groups are known to the person skilled in the art. Preferably, the dicarboxylic acids which can be used are succinic acid, glutaric acid, adipic acid, sebacic acid, o-phthalic acid, their isomers and hydrogenation products, and esterifiable derivatives, such as anhydrides, e.g. maleic anhydride, or dialkyl esters of said acids. A suitable polycarboxylic acid is, for example, trimellitic acid. Polyesterols to be used also include polycaprolactone diols and triols, the preparation of which is likewise known to the person skilled in the art.

Preferred hydroxy compounds are saturated polyesters comprising at least 2, in particular 2 to 6, free hydroxyl groups which can, if appropriate, also comprise ether groups or polyethers (as component bx)) with at least 2, in particular 2 to 6, free hydroxyl groups.

The components bix), such as, for example, polyester (meth)acrylates have at least 2 free-radically polymerizable double bonds per molecule. It is also preferred to use mixtures of, for example, polyester (meth)acrylates which comprise, on average, more than 2 free-radically polymerizable, olefinally unsaturated double bonds per molecule of polyester (meth)acrylate. Such mixtures arise, for example, by mixing compounds with in each case 2 and compounds with in each case 3 or more polymerizable double bonds per molecule. Compounds which comprise only one or no double bond per molecule may of course also be present in the mixtures. Such compounds are then present, however, in amounts such that the average number of polymerizable double bonds per molecule is nevertheless more than 2.

bx) Polyethers comprising at least two free-radically polymerizable, olefinally unsaturated double bonds The term polyethers is known to the person skilled in the art. Polyethers are polymers whose repeat units are joined by ether functionalities (C—O—C). Examples of polyethers are polyalkylene glycols (polyethylene glycols, polypropylene glycols, polyepichlorohydrins) as polymers of 1,2-epoxides, epoxide resins, polytetrahydrofurans (polytetramethylene glycols), polyoxetanes, polyphenylene ethers (polyaryl ethers) or polyether (ether) ketone (ketone)s.

Components bx) according to this invention are, for example, polyether (meth)acrylates which comprise at least two free-radically polymerizable double bonds per molecule. These are known to the person skilled in the art. They can be prepared by various methods. For example, polyethers containing hydroxyl groups which are esterified with acrylic acid and/or methacrylic acid to give the polyether (meth)acrylates can be obtained by reacting di- and/or polyhydric alcohols with various amounts of ethylene oxide and/or propylene oxide by well known methods (cf. e.g. Houben-Weyl, volume XIV, 2, Macromolecular Substances II, (1963)). It is also possible to use polymerization products of tetrahydrofuran or butylene oxide. DE 2 853 921, to which reference is made here in its entirety, also describes suitable components bx), such as, for example, aliphatic or aromatic-aliphatic polyethers which are obtained by reacting di- and/or polyhydric alcohols with various amounts of ethylene oxide and/or propylene oxide and whose free hydroxyl groups are completely or partially etherified with ethylenically unsaturated alcohols, for example allyl alcohol, methallyl alcohol, crotyl alcohol, cinnamyl alcohol, and/or esterified with α,β-ethylenically unsaturated monocarboxylic acids.

Polyether acrylates suitable as component bx) are, for example, also described in EP-A 0 279 303, to which reference is hereby made in its entirely. These polyether acrylates are obtainable by reacting A) 1 equivalent of a 2- to 6-hydric oxalkylated $C_2$-$C_{10}$-alcohol with B) 0.05 to 1 equivalent of a 2- to 4-basic $C_2$- to $C_{10}$-carboxylic acid or anhydrides thereof and C) 0.1 to 1.5 equivalents of acrylic acid and/or methacrylic acid, and reaction of the excess carboxyl groups with the equivalent amount of an epoxide compound.

EP-A 0 686 621, to which reference is made here in its entirety, also describes suitable components bx). These are reaction products of (meth)acrylic acid with a hydroxy compound. Suitable hydroxy compounds are compounds with one or more hydroxy groups. Mention may be made, for example, of compounds comprising hydroxy groups and alkoxylated with ethylene oxide or propylene oxide.

Preferred hydroxy compounds are saturated polyethers with at least 2, in particular 2 to 6, free hydroxyl groups. Suitable polyethers containing hydroxyl groups are, for example, those which can be obtained by known methods by reacting di- and/or polyhydric alcohols with various amounts of ethylene oxide and/or propylene oxide. In the case of the ethylene glycol/propylene glycol mixed condensation products, the reaction can expediently be controlled so that predominantly primary hydroxyl groups arise in terminal position. Likewise, polymerization products of tetrahydrofuran or butylene oxide which comprise hydroxyl groups can also be used.

Examples of component bx) are polyalkylene glycol (meth)acrylates.

In one preferred embodiment of the invention, the components bx) used are those compounds whose molecular weight $M_w$ is at least 200 g/mol, particularly preferably at least 400 g/mol, very particularly preferably at least 500 g/mol and most preferably more than 700 g/mol.

In a further preferred embodiment of the invention, the components b) used are compounds bix) and/or bx) or mixtures of compounds bix) and/or bx), where the average number of olefinic, free-radically polymerizable double bonds per molecule is more than 2. Such mixtures are formed, for example, by mixing compounds with in each case 2 and compounds with in each case 3 or more polymerizable double bonds per molecule. Compounds which comprise only one or no double bond per molecule can of course also be present in the mixtures. Such compounds are then, however, present in amounts such that the average number of polymerizable double bonds per molecule is nevertheless more than 2.

It should be emphasized at this point that there are compounds suitable as component b) which can be assigned to both groups bix) and bx) since they comprise both ester groups and ether groups. Commercially available products which are suitable as component b) are, for example:

Photomer®5010, Photomer®5429, Photomer®5430, Photomer®5432, Photomer®5662, Photomer®5806, Photomer®5930 from Cognis;

the Resin® grades from UCB such as, for example, Resin®80, 81, 83, 450, 657, 770, 809, 810, 830, 835, 870, 1657, 1810, 1870, 2047**, 2870;

the CN® grades from Sartomer, such as, for example, CN293, CN294, CN296, CN292, CN2297A, CN2279, CN2280, CN2470, CN295, CN2300, CN2200, CN2203, CN2282, CN2284, CN2270, CN2271, CN2272, CN2273, CN2276, CN2250, CN2251, CN2252, CN2253, CN2255, CN2256, CN2257, CN2258, CN2259, CN2260, CN2261;

AROPLAZ®4097-WG4-55 from Reichhold;

Syntholux®-PE grades from Synthopol as polyester acrylates and the Syntholux®-PA grades from Synthopol as polyether acrylates;

Laromer® grades Laromer®PE 55F, Laromer®PE 56F, Laromer®PE 46T, Laromer®9004, Laromer®PE 44F, Laromer®8800, Laromer®LR 8981. Laromer®LR 8992, Laromer®PE 22WN, Laromer®PE 55WN, Laromer®33F, Laromer®LR 8863, Laromer®PO 43F, Laromer®LR 8967, Laromer®LR 8982, Laromer®LR 9007 (BASF).

bxi) Compounds with at least two free-radically polymerizable double bonds

Suitable components b) are also compounds with at least two free-radically polymerizable, olefinically unsaturated double bonds per molecule. Such compounds are usually referred to as crosslinkers. Free-radically polymerizable, olefinically unsaturated double bonds are, for example, alkenyl groups, which are formally formed by removing an H atom from an alkene. These include vinyl (—CH=CH$_2$), 1-propenyl (—CH=CH—CH$_3$), 2-propenyl or allyl (—CH$_2$—CH=CH$_2$), 1-butenyl (—CH=CH—CH$_2$—CH$_3$) etc.

Alkylidene groups, i.e. groups which are joined to a carbon atom of a molecule by a double bond also belong to the free-radically polymerizable, olefinically unsaturated double bonds (example ethylidene: =CHCH$_3$).

Suitable crosslinkers are, for example, acrylic esters, methacrylic esters, allyl ethers or vinyl ethers of at least dihydric alcohols. The OH groups of the parent alcohols may here be completely or partially etherified or esterified; however, the crosslinkers comprise at least two olefinically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic neopentyl glycol monoester, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetrahydrofurans with molecular weights of in each case 200 to 10 000.

Apart from the homopolymers of ethylene oxide and propylene oxide, it is also possible to use block copolymers of ethylene oxide or propylene oxide or copolymers which comprise ethylene oxide and propylene oxide groups in incorporated form. Examples of parent alcohols with more than two OH groups are trimethylolpropane, glycerol, pentaerythritol. 1,2,5-pentanetriol, 1,2,6-hexanetriol, triethoxycyanuric acid, sorbitan, sugars, such as saccharose, glucose, mannose. The polyhydric alcohols can of course also be used following reaction with ethylene oxide or propylene oxide as the corresponding ethoxylates or propoxylates, respectively. These polyhydric alcohols can also firstly be converted to the corresponding glycidyl ethers by reaction with epichlorohydrin.

Further suitable crosslinkers are the vinyl esters or the esters of monohydric, unsaturated alcohols with ethylenically unsaturated C3-C6-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, it is also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers are esters of unsaturated carboxylic acids with the polyhydric alcohols described above, for example oleic acid, crotonic acid, cinnamic acid or 10-undecenoic acid.

Suitable crosslinkers are, furthermore, straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Also suitable as crosslinkers are acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids, as have been described above.

Also suitable as crosslinkers are triallylamine and triallylmonoalkylammonium salts, e.g. triallylmethylammonium chloride or methyl sulfate.

Also suitable are N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropyleneurea.

Also suitable are alkylenebisacrylamides, such as methylenebisacrylamide and N,N'-(2,2-)butane and 1,1'-bis(3,3'-vinylbenzimidazolith-2-one)-1,4-butane.

Other suitable crosslinkers are, for example, alkylene glycol di(meth)acrylates such as ethylene glycol diacrylate, ethylene glycol dimethacrylate, tetraethylene glycol acrylate, tetraethylene glycol dimethacrylate, diethylene glycol acrylate, diethylene glycol methacrylate, vinyl acrylate, allyl acrylate, allyl methacrylate, divinyldioxane, pentaerythritol allyl ether, and mixtures of these crosslinkers.

Further suitable crosslinkers are divinyldioxane, tetraallylsilane or tetravinylsilane. Particularly preferably used crosslinkers are, for example, methylenebisacrylamide, triallylamine and triallylalkylammonium salts, divinylimidazole, pentaerythritol triallyl ether, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin.

Very particularly preferred crosslinkers are allyl methacrylate, pentaerythritol triallyl ether, methylenebisacrylamide, N,N'-divinylethyleneurea, triallylamine and triallylmonoalkylammonium salts, and acrylic esters of glycol, butanediol, trimethylolpropane or glycerol or acrylic esters of glycol, butanediol, trimethylolpropane or glycerol reacted with ethylene oxide and/or epichlorohydrin.

bxii) (meth)acrylamides different from aii), such as, for example, acrylamide, (meth)acrylamide, N-methyl(meth)acrylamide, N-ethyl(meth)acrylamide, N-n-propyl(meth)acrylamide and N-isopropyl(meth)acrylamide.

Preferred compounds b) are anionic or anionogenic compounds bi), compounds bii) or biv) carrying amino groups, water-soluble, nonionic compounds bvi), compounds carrying urethane groups bvii), polyesters bix), polyethers bx) and mixtures thereof.

Solution Polymerization

According to the invention, the polymers are prepared by solution polymerization in a solvent comprising alcohol which comprises water in the range from 5 to 50% by weight.

Suitable alcohols are, for example, methanol, ethanol, n-propanol, isopropanol, n-butanol, sec.-butanol, tert-butanol, 3-methyl-1-butanol (isoamyl alcohol), n-hexanol, cyclohexanol or glycols, such as ethylene glycol, propylene glycol and butylene glycol, and alkyl ethers of polyhydric alcohols, such as diethylene glycol, triethylene glycol, polyethylene glycols with number-average molecular weights up to about 3000, glycerol and dioxane.

The solvent particularly preferably comprises ethanol and/or isopropanol, in particular ethanol.

In addition to alcohol and water, further solvents can be used. Of suitability in principle are all for the free-radical polymerization, such as, for example, acetone, acetonitrile, aniline, anisole, benzonitrile, tert-butyl methyl ether (TBME), gamma-butyrolactone, quinolene, chloroform, cyclohexane; diethyl ether, dimethylacetamide, dimethylformamide, dimethyl sulfoxide, dioxane, glacial acetic acid, acetic anhydride, ethyl acetate, ethylene dichloride, ethylene glycol dimethyl ether, formamide, hexane, methylene chloride, methyl ethyl ketone, N-methylformamide, petroleum ether/light benzine, piperidine, propylene carbonate (4-methyl-1,3-dioxol-2-one), sulfolane, tetrachloroethene, tetrachloromethane, tetrahydrofuran, toluene, 1,1,1-trichloroethane, trichloroethene, triethylene glycol dimethyl ether (triglyme).

Preferably, the solvent comprises water in the range from 8 to 45% by weight, particularly preferably 15 to 45% by weight.

Preferably, the solvent comprises ethanol and/or isopropanol in the range from 55 to 92% by weight, particularly preferably 55 to 85% by weight.

Preference is given to a method according to the invention in which the temperature at which the polymerization is carried out is in the range from 30 to 120° C., preferably from 40 to 100° C.

If the amount of monomer a) used for the polymerization is at least 70% by weight of the amount of the monomers used overall, it is advantageous if the weight ratio of water to alcohol is greater than 1:2.

The polymerization usually takes place under atmospheric pressure, although it can also proceed under reduced or increased pressure. A suitable pressure range is between 1 and 10 bar.

If the monomer composition to be polymerized comprises more basic groups than acid groups, then it is advantageous to reduce the pH of the polymerization solution by adding acids.

If vinyllactams bvi) are used as compounds b), then the pH is kept at a value of at least 6, preferably in the range from 6 to 8, before and during the polymerization.

At least one of the initiators used for the method according to the invention is an ethanol-soluble initiator.

Ethanol-soluble means that, at a pressure of 1 bar and a temperature of 20° C. and 1013 mbar, at least 1 g, preferably at least 5 g and in particular at least 10 g of the particular initiator can be dissolved in 1 liter of ethanol to give a clear solution.

Preferably, the initiator is chosen from ethanol-soluble diazo and peroxide compounds. Examples of such initiators are diacetyl peroxide, dibenzoyl peroxide, succinyl peroxide, di-tert-butyl peroxide, tert-butyl perbenzoate, tert-butyl perpivalate, tert-butyl peroctoate, tert-butyl peroxy-2-ethylhexanoate, tert-butyl permaleinate, benzoyl peroxide, tert-amyl peroxipivalate, cumene hydroperoxide, diisopropyl peroxidicarbamate, bis-(o-toluoyl)peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, 2,2'-azobis(2-methylpropionamide) dihydrochloride (Wako®V50), dimethyl 2,2'-azobis(2-methylpropionate) or 2,2'-azobis(2-methyl-butyronitrile).

The polymerization initiator is preferably chosen from the group consisting of benzoyl peroxide, tert-amyl peroxipivalate, 2,2'-azobis(2-methylpropionamide) dihydrochloride, dimethyl 2,2'-azobis(2-methylpropionate), 2,2'-azobis(2-methylbutyronitrile), 2,2'-azobis(2-methylpropionamide).

Suitable initiators are also 2,2'-azobis(4-methoxy-2,4-dimethylvaleronitrile), 2,2'-azobis(2,4-dimethylvaleronitrile), dimethyl 2,2'-azobis(2-methylpropionate), 2,2'-azobis(2-methylbutyronitrile), 1,1'-azobis(cyclohexane-1-carbonitrile), 2,2'-azobis[N-(2-propenyl)-2-methylpropionamide], 1-[(cyano-1-methylethyl)azo]formamide, 2,2'-azobis(N-butyl-2-methylpropionamide), 2,2'-azobis(N-cyclohexyl-2-methylpropionamide). The abovementioned azo initiators are commercially available under the Wako®V grades.

The amount of the at least one ethanol-soluble initiator used for the polymerization of the monomers is preferably from 0.001 to 2.5% by weight, particularly preferably 0.01 to 1.5% by weight and in particular 0.05 to 1.0% by weight, based on the total amount of the monomers used.

In one embodiment of the invention, both at least one ethanol-soluble initiator and at least one water-soluble initiator are used in the method according to the invention. A water-soluble polymerization initiator is understood as meaning an initiator which dissolves to give a clear solution at 20° C. and 1013 mbar to at least 1 g, preferably to at least 5 g and in particular to at least 10 g in 1 liter of water.

Water-soluble polymerization initiators are chosen from the group consisting of peroxides, hydroperoxides, peroxodisulfates, percarbonates, peroxide esters, azo compounds and mixtures thereof.

In one embodiment of the invention, the water-soluble polymerization initiator used in addition to the ethanol-soluble initiator is preferably chosen from the group consisting of water-soluble azo compounds, hydrogen peroxide, lithium peroxodisulfate, sodium peroxodisulfate, potassium peroxodisulfate, ammonium peroxodisulfate, and mixtures thereof.

In addition, the water-soluble polymerization initiator used in addition to the ethanol-soluble initiator is chosen from the group consisting of 2,2'-azobis[2-(5-methyl-2-imidazolin-2-yl)propane]dihydrochloride
2,2'-azobis[2-(2-imidazolin-2-yl)propane]dihydrochloride
2,2'-azobis[2-(2-imidazolin-2-yl)propanedisulfate dihydrate
2,2'-azobis(2-methylpropionamide) dihydrochloride
2,2'-azobis[N-(2-carboxyethyl)-2-methylpropionamidine] tetrahydrate
2,2'-azobis[2-(3,4,5,6-tetrahydropyrimidin-2-yl)propane]dihydrochloride
2,2'-azobis{2-[1-(2-hydroxyethyl)-2-imidazolin-2-yl]propane}dihydrochloride
2,2'-azobis[2-(2-imidazolin-2-yl)propane]
2,2'-azobis{2-methyl-N-[1,1-bis(hydroxymethyl)-2-hydroxyethyl]propionamide
2,2'-azobis{2-methyl-N-[2-(1-hydroxybutyl)]propionamide}
2,2'-azobis[2-methyl-N-(2-hydroxyethyl)propionamide] and mixtures thereof.

To adjust the molecular weight, the polymerization can take place in the presence of at least one regulator. Regulators which may be used are the customary compounds known to the person skilled in the art, such as, for example, sulfur compounds, e.g. mercaptoethanol, 2-ethylhexyl thioglycolate, thioglycolic acid or dodecyl mercaptan, and tribromochloromethane or other compounds which have a regulating effect on the molecular weight of the polymers obtained. A preferred regulator is cysteine.

The amounts of compounds to be polymerized, based on solvent, are preferably chosen so that solutions with a solids content of from 25 to 80% by weight are obtained. The solution polymerization can be carried out either as a batch process or in the form of a feed method, including monomer feed, step procedure and gradient procedure. In general, preference is given to the feed method in which, if appropriate, some of the polymerization mixture is initially introduced and heated to the polymerization temperature, and then the remainder of the polymerization mixture is introduced, usually via one or more, spatially separate feeds, continuously, stepwise or with overlap of a concentration gradient while maintaining the polymerization of the polymerization zone.

In order to achieve the purest possible polymers with a low residual monomer content, the main polymerization can, as already described above, be followed by an afterpolymerization. The afterpolymerization can take place in the presence of a likewise ethanol-soluble or preferably a water-soluble initiator.

In one preferred embodiment of the invention, at least one ethanol-soluble initiator is used for the main polymerization, and at least one water-soluble initiator is used for the afterpolymerization. The main polymerization is deemed to be complete when the residual monomer content is at most 10% by weight, preferably at most 5% by weight, particularly preferably at most 2% by weight and in particular at most 1% by weight, based on the solids content of the polymerization mixture.

One preferred embodiment of the invention is thus the method according to the invention wherein the polymerization is carried out until a residual monomer content of at most 10% by weight, preferably at most 5% by weight, particularly preferably at most 2% by weight and in particular at most 1% by weight (main polymerization) is achieved, based on the solids content of the polymerization mixture, in the presence of at least one ethanol-soluble initiator, and the afterpolymerization following the main polymerization is carried out in the presence of at least one water-soluble initiator.

Preferably, the afterpolymerization takes place at least at the same temperature, preferably at a higher temperature, than the main polymerization. If desired, the reaction mixture can be subjected to stripping with steam or steam distillation after the polymerization or between the first and second polymerization steps.

The monomers used for the polymerization are preferably reacted to at least 95%, particularly preferably to at least 99% and in particular to at least 99.9% (degree of polymerization).

The polymers present in solution after the polymerization can be converted into powders by customary drying methods known to the person skilled in the art. Preferred methods are, for example, spray-drying, fluidized-bed drying, drum drying and belt drying. Freeze-drying and freeze-concentration can likewise be used. If desired, the solvent can also be removed, completely or in part, by customary methods, e.g. distillation at reduced pressure.

A preferred embodiment of the invention is the method according to the invention wherein the isopropanol used as solvent constituent is essentially completely removed after the polymerization, removal preferably taking place by distillation.

If, for the preparation according to the invention of the polymers, n-vinylpyrrolidone is used as monomer b) and ethanol is used as solvent constituent, then it is advantageous if the ethanol is essentially completely removed after the polymerization.

To "essentially" remove a constituent is understood as meaning removal of the constituent originally present in the solvent to a residual content of at most 10% by weight, preferably at most 5% by weight and in particular at most 1% by weight, of this constituent, based on the total polymerization mixture.

If a distillation is to be carried out to remove the alcoholic solvent, then it is advantageous to adjust the pH of the polymerization solution after the polymerization to a value of 6.5 or less, preferably to a value between 4 and 6.5.

The solids content of the polymerization solution, i.e. the amount of all components present, with the exception of the solvents, is preferably at least 20% by weight, particularly preferably at least 25% by weight and in particular at least 30% by weight.

The polymers produced by the method according to the invention may be anionic or anionogenic polymers. For use in cosmetic preparations, it is advantageous if the acid groups of these polymers are partially or completely neutralized with a base since the resulting salts of the polymers usually have better solubility or dispersibility in water than unneutralized polymers. Bases which can be used for neutralizing these polymers are alkali metal bases, such as sodium hydroxide solution, potassium hydroxide solution, sodium carbonate, sodium hydrogen carbonate, potassium carbonate or potassium hydrogen carbonate and alkaline earth metal bases, such as calcium hydroxide, calcium oxide, magnesium hydroxide or magnesium carbonate, and ammonia and amines. Suitable amines are, for example, $C_1$-$C_6$-alkylamines, preferably n-propylamine and n-butylamine, dialkylamines, preferably diethylpropylamine and dipropylmethylamine, trialkylamines, preferably triethylamine and triisopropylamine, $C_1$-$C_6$-alkyldiethanolamines, preferably methyl- or ethyldiethanolamine and di-$C_1$-$C_6$-alkylethanolamines. Particularly for use in hair-treatment compositions, 2-amino-2-methyl-1-propanol, 2-amino-2-ethylpropane-1,3-diol, diethylaminopropylamine, triethanolamine and triisopropanolamine have proven useful for neutralizing polymers comprising acid groups. The neutralizing agent may, for example, also be or comprise 2-amino-2-methyl-1-propanol or a mixture of 2-amino-2-methyl-1-propanol and triethanolamine. Neutralization of the polymers comprising acid groups can also be carried out with the help of mixtures of two or more bases, e.g. mixtures of sodium hydroxide solution or potassium hydroxide solution.

Depending on the intended use, neutralization can be carried out partially, e.g. to 5 to 95%, preferably 30 to 95%; or completely, i.e. to 100%. In addition, the neutralizing agent can also be added in a more than equivalent amount.

Cosmetic Preparations

Stricter environmental regulations and a growing ecological awareness increasingly demand ever lower fractions of volatile organic components (VOCs) in cosmetic aerosol preparations such as, for example, aerosol hair sprays.

The VOC content in hair sprays is essentially determined by the nonaqueous solvents and the propellants. For this reason, instead of nonaqueous solvents, recourse is currently and increasingly being made to water as solvent. However, this replacement of the organic solvents entails a number of problems. Thus, formulations of the film-forming polymers known from the prior art which satisfy the corresponding VOC regulations are not, for example, sprayable, or are only sprayable following further dilution and are thus only of limited suitability for use in hair sprays. Polymer films which are formed from such preparations sometimes do not have the required mechanical quality and thus have inadequate setting effect and poor hold for the hair.

The copolymers produced by the method according to the invention are exceptionally suitable for producing cosmetic, in particular skin cosmetic and/or hair cosmetic, preparations. They serve here, for example, as polymeric film formers. They can be used and formulated universally in a very wide variety of cosmetic, preferably hair cosmetic, preparations and are compatible with customary additional components.

The copolymers are advantageously suitable for producing elastic hairstyles coupled with strong hold, even at high atmospheric humidity. In aerosol formulations, the copolymers are notable for good propellant gas compatibility, good solubility in aqueous/alcoholic solvent mixtures, in particular for the suitability for use as optically clear low-VOC formulations and for good ability to be washed out and ability to be combed out without flaking effect. In addition, they improve hair treated therewith in its sensorially perceptible properties, such as feel, volume or handleability. Hair spray formulations based on the copolymers produced by the method according to the invention are notable for good sprayability and good rheological properties and extremely low stickiness of the resulting films. The cosmetic, preferably hair cosmetic, preparations comprising the copolymers do not have a tendency for foaming following application. Besides the good compatibility with the customary cosmetic ingredients, the applied copolymer films dry rapidly.

The present invention accordingly further provides the use of the copolymers obtainable by the method according to the invention in cosmetic preparations, and also such cosmetic preparations per se.

Cosmetically Acceptable Carrier B

The cosmetic preparations are preferably aqueous preparations which comprise at least 10% by weight, preferably at least 20% by weight and particularly preferably at least 30% by weight, of water. Preferably, the cosmetic preparations according to the invention comprise at most 80% by weight (VOC-80), preferably at most 55% by weight (VOC-55) of volatile organic constituents.

The invention accordingly provides cosmetic preparations in which the fraction of volatile organic components is at most 55% by weight, based on the cosmetic preparation. Besides water and the copolymers obtainable by the method according to the invention, the cosmetic preparations further have at least one cosmetically acceptable carrier B which is chosen from i) water-miscible organic solvents, preferably $C_2$-$C_4$-alkanols, in particular ethanol,
ii) oils, fats, waxes,
iii) esters of $C_6$-$C_{30}$-monocarboxylic acids with mono-, di- or trihydric alcohols different from ii),
iv) saturated acyclic and cyclic hydrocarbons,
v) fatty acids,
vi) fatty alcohols,
vii) propellants (propellant gases) and
viii) mixtures thereof.

Suitable carriers B and further active ingredients and additives to be used advantageously are described in detail below.

Suitable cosmetically and pharmaceutically compatible oil and fat components are described in Karl-Heinz Schrader, Grundlagen und Rezepturen der Kosmetika [Fundamentals and Formulations of Cosmetics], 2nd edition, Verlag Hüthig, Heidelberg, pp. 319-355, to which reference is hereby made.

As cosmetically acceptable carrier B, the cosmetic preparations can, for example, have an oil or fat component which is chosen from: hydrocarbons of low polarity, such as mineral oils; linear saturated hydrocarbons, preferably having more than 8 carbon atoms, such as tetradecane, hexadecane, octadecane etc.; cyclic hydrocarbons, such as decahydronaphthalene; branched hydrocarbons; animal and vegetable oils; waxes; wax esters; vaseline; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example, under the name cyclomethicone.

Preferred oil or fat components B) are chosen from paraffin and paraffin oils; vaseline; natural fats and oils, such as castor oil, soya oil, peanut oil, olive oil, sunflower oil, sesame oil, avocado oil, cocoa butter, almond oil, peach kernel oil, ricinus oil, cod-liver oil, pig fat, spermaceti, spermaceti oil, sperm oil, wheat germ oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candelilla wax, spermaceti, and mixtures of the abovementioned oil and fat components.

Suitable hydrophilic carriers 8) are chosen from water, 1-, 2- or polyhydric alcohols having preferably 1 to 8 carbon atoms, such as ethanol, n-propanol, isopropanol, propylene glycol, glycerol, sorbitol, etc.

The cosmetic preparations may be skin cosmetic, hair cosmetic or dermatological, hygiene or pharmaceutical preparations. On account of their film-forming and flexible properties, the copolymers which can be produced by the method according to the invention are particularly suitable as additives for hair cosmetics and skin cosmetics. Preferably, the cosmetic preparations which comprise the copolymers according to the invention are in the form of spray, gel, foam, ointment, cream, emulsion, suspension, lotion, milk or paste. If desired, liposomes or microspheres can also be used.

Preferably, the cosmetic compositions according to the invention comprise at least one copolymer according to the invention, at least one carrier B as defined above and at least one constituent different therefrom which is preferably chosen from cosmetically active ingredients, emulsifiers, surfactants, preservatives, perfume oils, thickeners, hair polymers, hair and skin conditioners, graft polymers, water-soluble or dispersible silicone-containing polymers, photoprotective agents, bleaches, gel formers, care agents, colorants, tinting agents, tanning agents, dyes, pigments, consistency regulators, humectants, refatting agents, collagen, protein hydrolyzates, lipids, antioxidants, antifoams, antistats, emollients and softeners.

The preparations according to the invention preferably have a pH of from 2.0 to 9.3. The pH range is particularly preferably between 4 and 8. Additional cosolvents which may be present are organic solvents or a mixture of solvents with a boiling point below 400° C. in an amount of from 0.1 to 15% by weight, preferably from 1 to 10% by weight. Particularly suitable additional cosolvents are unbranched or branched hydrocarbons, such as pentane, hexane, isopentane and cyclic hydrocarbons, such as cyclopentane and cyclohexane. Further particularly preferred water-soluble solvents are glycerol, ethylene glycol and propylene glycol in an amount up to 30% by weight.

In one preferred embodiment of the invention, the cosmetic preparations have a fraction of volatile organic components of at most 80% by weight, preferably at most 55% by weight and in particular at most 35% by weight. A preferred subject matter is thus cosmetic, preferably hair cosmetic, preparations which correspond to the low-VOC standard, i.e. VOC-80 or VOC-55 standard.

Preference is given to the use of the copolymers, in particular in hair spray preparations, which comprise the following constituents:
   partially or completely neutralized copolymer according to the invention;
   water;
   cosmetically customary organic solvent, such as, for example, ethanol, isopropanol and dimethoxymethane, in addition also acetone, n-propanol, n-butanol, 2-methoxypropan-1-ol, n-pentane, n-hexane, cyclohexane, n-heptane, n-octane or dichloromethane or mixtures thereof;
   cosmetically customary propellant, such as, for example, n-propane, isopropane, n-butane, isobutane, 2,2-dimethylbutane, n-pentane, isopentane, dimethyl ether, difluoroethane, fluorotrichloromethane, dichlorodifluoromethane or dichlorotetrafluoroethane, HFC-152 A (1,1-difluoroethane), HFC-134a (1,1,2,2-tetrafluoroethane), $N_2$, $N_2O$ and CO or mixtures thereof.

For neutralizing the copolymers obtainable by the method according to the invention and for adjusting the pH of the cosmetic, preferably hair cosmetic, preparations, alkanolamines are advantageously used. Examples are aminomethylpropanol, diethanolamine, diisopropanolamine, ethanolamine, methylethanolamine, N-lauryldiethanolamine, triethanolamine and triisopropanolamine. It is possible to use alkanolamines carrying either primary amino groups or secondary amino groups.

Furthermore, alkali metal hydroxides (e.g. NaOH, preferably KOH) and other bases can be used for the neutralization (e.g. histidine, arginine, lysine or ethylenediamines, diethylenetriamine, melamine, benzoguanamine). All of the stated bases can be used on their own or as a mixture with other bases for the neutralization of acid-containing cosmetic products.

In one preferred embodiment of the invention, amines comprising hydroxyl groups from the group consisting of N,N-dimethylethanolamine, N-methyldiethanolamine, triethanolamine, 2-amino-2-methylpropanol and mixtures thereof are chosen for the neutralization.

Here, alkanolamines carrying secondary or tertiary amino groups may exhibit advantageous effects.

The present invention accordingly provides aqueous cosmetic, preferably skin cosmetic and/or hair cosmetic, preparations which, besides the at least one copolymer obtainable by the method according to the invention and the carrier B, comprise at least also one active ingredient or additive chosen from the group consisting of viscosity-modifying substances, hair care substances, hair-setting substances, silicone compounds, photoprotective substances, fats, oils, waxes, preservatives, pigments, soluble dyes, particulate substances and surfactants.

In one preferred embodiment, such hair cosmetic formulations comprise
i) 0.05 to 20% by weight of at least one copolymer as described above,
ii) 20 to 99.95% by weight of water and/or alcohol,
iii) 0 to 50% by weight of at least one propellant gas,
iv) 0 to 5% by weight of at least one emulsifier,
v) 0 to 3% by weight of at least one thickener, and
vi) up to 25% by weight of further constituents.

Alcohol is understood as meaning all of the abovementioned alcohols customary in cosmetics, preferably ethanol, isopropanol, n-propanol.
Propellants (Propellant Gases)

Of the specified compounds, the propellants (propellant gases) used are primarily the hydrocarbons, in particular propane, n-butane, n-pentane and mixtures thereof, and also dimethyl ether and difluoroethane. If appropriate, one or more of the specified chlorinated hydrocarbons are co-used in propellant mixtures, but only in small amounts, for example up to 20% by weight, based on the propellant mixture.

The cosmetic preparations are also particularly suitable for pump spray preparations without the addition of propellants or else for aerosol sprays with customary compressed gases such as nitrogen, compressed air or carbon dioxide as propellant. A water-containing standard aerosol spray formulation comprises, for example, the following constituents:
   copolymer neutralized to 100%
   alcohol
   water
   dimethyl ether and/or propane/n-butane and/or propane/isobutane, Here, the total amount of volatile organic components is preferably at most 80% by weight, particularly preferably at most 55% by weight, of the preparation.

Preferably, the cosmetic preparations comprise at least one copolymer as described above, at least one cosmetically acceptable carrier B as defined above and at least one further active ingredient or additive different therefrom which is chosen from cosmetically active ingredients, emulsifiers, surfactants, preservatives, perfume oils, thickeners, hair polymers, hair conditioners, graft polymers, water-soluble or dispersible silicone-containing polymers, photoprotective agents, bleaches, gel formers, care agents, colorants, tinting agents, tanning agents, dyes, pigments, consistency regulators, humectants, refatting agents, collagen, protein hydrolyzates, lipids, antioxidants, antifoams, antistats, emollients, lanolin components, protein hydrolyzates and softeners.
Further Polymers In order to adjust the properties of cosmetic preparations in a targeted way, it may be advantageous to use the copolymers described above in a mixture with further (hair) cosmetically customary polymers.

In a further preferred embodiment, the cosmetic preparation comprises 0.01 to 15% by weight, preferably 0.5 to 10% by weight, of at least one further synthetic or natural nonionic, preferably a film-forming polymer. Natural polymers are also understood as meaning chemically modified polymers of natural origin. Film-forming polymers are understood as meaning those polymers which, when applied in 0.01 to 5% strength aqueous, alcoholic or aqueous-alcoholic solution, are able to deposit a polymer film on the hair.

Suitable as such further customary polymers for this purpose are, for example, anionic, cationic, amphoteric, zwitterionic and neutral polymers. Such polymers are known to the person skilled in the art and require no further explanation.

EXAMPLES

The following examples are intended to illustrate the invention without limiting it thereto
Abbreviations Used:
t-BA tert-butyl acrylate
MAA methacrylic acid
AA acrylic acid
NtBAEMA N-tert-butylaminoethyl methacrylate
VP N-vinylpyrrolidone
MMA methyl methacrylate
DMAEMA dimethylaminoethyl methacrylate
t-BMA tert-butyl methacrylate
i-BMA isobutyl methacrylate
EMA ethyl methacrylate
SMA stearyl methacrylate
UDA urethane diacrylate[1])
UA3 urethane acrylate 3
Si-UA DE 198 38 852, Tab.1, Ex. No. 2
iPrOH isopropanol
EtOH ethanol
dem. completely demineralized
V59 initiator Wako®V59
TBPP tert-butyl perpivalate
TBPO tert-butyl peroctoate
NaPS sodium peroxodisulfate
AMP 2-amino-2-methylpropanol
Preparation of Urethane Acrylate 3

In a round-bottomed flask, 672.0 g of a polyester of adipic acid and neopentyl glycol with an OH number of about 200, 140.0 g of hydroxyethyl acrylate, 0.6 g of hydroquinone monomethyl ether, 1.21 g of 2,6-di-tert-butyl-4-methylphenol were initially introduced and heated to 50° C. Then, 400.0 g of isophorone diisocyanate were added dropwise over the course of 30 minutes. The mixture was left to react for a further 20 hours at 90-95° C., during which the NCO content dropped to 0.1%. It was cooled to 60° C., then 10.0 g of methanol were added and the mixture was left to further react for about 4 hours at 90-95° C. until the isocyanate content (NCO value) had dropped to 0. The resin obtained was mixed at room temperature with 510.0 g of tripropylene glycol diacrylate and filtered over a 50 μm filter and bottled.
Preparation of Urethane Acrylate A In a round-bottomed flask, 672.0 g of a polyester of adipic acid and neopentyl glycol with a OH number of about 200, 140.0 g of hydroxyethyl acrylate, 0.6 g of hydroquinone monomethyl ether, 1.20 g of 2,6-di-tert-butyl-4-methylphenol, 0.12 g of tetrabutyl orthotitanate were initially introduced and heated to 50° C. 400.0 g of isophorone diisocyanate were then added dropwise over the course of 30 minutes. The mixture was left to react for a further 7 hours at 90-95° C., during which the NCO content dropped to 0.56%. It was cooled to 60° C., then 520.0 g of ethanol were added and it was left to react further for about 2 hours at 65-70° C. until the isocyanate content (NCO value) had dropped to 0. The resin obtained was filtered over a 50 μm filter and bottled.

Preparation of Copolymer According to Example 1

Polymer of t-BA, MAA and AA in the weight ratio 75:20:5

| Initial charge | 100 g | dem. water |
| | 200 g | ethanol |
| | 35 g | feed 1 |
| | 5 g | feed 2 |
| Feed 1 | 300 g | tert-butyl acrylate |
| | 80 g | MAA |
| | 20 g | AA |
| | 225 g | ethanol |
| Feed 2 | 120 g | ethanol |
| | 6 g | Wako ® V59 (manufacturer: Wako Pure Chemical Industries Ltd.) |
| Feed 3 | 180 g | ethanol |
| | 8 g | tert-butyl perpivalate |
| Feed 4 | 118 g | AMP (90% strength) |
| | 112 g | water |

The initial charge was heated to 75° C. under a nitrogen atmosphere. Feeds 1 and 2 were added over the course of 3 hours. The polymer solution was further stirred for a further 2 hours at 78° C. Feed 3 was metered in over 30 min and then the mixture was stirred for a further 5 h at 80° C. Finally, feed 4 was added and the mixture was neutralized for 30 min.

Approximately 10% by weight of the ethanol used were distilled off at a bath temperature of 120° C. and a transition temperature of about 80° C. Then, the amount of ethanol removed by distillation was added again to the solution in the form of fresh ethanol. The polymers as in examples 2, 3 and 9 were prepared analogously.

Preparation of Copolymer as in Example 5

Polymer of t-BA, MAA, VP, DMAEMA in the weight ratio 52:3:27:18

| Initial charge | 200 g | dem. water |
| | 265 g | ethanol |
| | 35 g | feed 1 |
| | 5 g | feed 2 |
| Feed 1 | 156 g | t-BA |
| | 108 g | VP |
| | 72 g | DMAEMA |
| | 12 g | MAA |
| | 200 g | ethanol |
| Feed 2 | 80 g | ethanol |
| | 4 g | Wako ® V59 |
| Feed 3 | 120 g | ethanol |
| | 6 g | tert-butyl perpivalate |
| Feed 4 | 115 g | lactic acid (90% strength) |
| | 67 g | water |
| Feed 5 | 400 g | ethanol |

The initial charge was heated to 75° C. under a nitrogen atmosphere. Feed 1 was added over the course of 4 hours and feed 2 was added over the course of 5 hours. The polymer solution was then stirred at 75° C. for a further 2 hours. Feed 3 was then metered in over 30 min and the solution was then stirred for a further 4 hours at 80° C. Finally, the mixture was neutralized by adding feed 4 over 20 min. At a bath temperature of 120° C., ethanol was distilled off until an internal temperature of 85° C. had been reached. Distillation was then carried out with steam until an internal temperature of about 100° C. had been reached. Finally, the mixture was cooled to about 40° C., then feed 5 was metered in and the mixture was stirred until a homogeneous phase was present. Water was added to reach a solids content of 30% by weight.

The polymers as in examples 6 and 7 were prepared analogously to this.

3.) Preparation of copolymer as in example 4:

Polymer of MMA, MAA, AA and DMAEMA in the weight ratio 73:12:12:3

| Initial charge | 215 g | dem. water |
| | 200 g | isopropanol |
| | 35 g | feed 1 |
| | 5 g | feed 2 |
| Feed 1 | 292 g | methyl methacrylate |
| | 48 g | MAA |
| | 48 g | AA |
| | 12 g | DMAEMA |
| | 225 g | isopropanol |
| Feed 2 | 75 g | isopropanol |
| | 7.8 g | Wako ® V59 |
| Feed 3 | 230 g | isopropanol |
| | 4 g | tert-butyl perpivalate |
| Feed 4 | 55 g | AMP |
| | 55 g | water |
| Feed 5 | 400 g | ethanol |

The initial charge was heated to 75° C. under a nitrogen atmosphere. Feed 1 was added over the course of 4 hours and feed 2 was added over the course of 5 hours. The polymer solution was then stirred at 75° C. for a further 2 hours. Feed 3 was then metered in over 30 min and the solution was then stirred for a further 4 hours at 80° C. Finally, the mixture was neutralized by adding feed 4 over 30 min. At a bath temperature of 120° C., ispropanol was distilled off until an internal temperature of 85° C. had been reached. Distillation was then carried out with steam until an internal temperature of about 100° C. had been reached.

Finally, the mixture was cooled to about 40° C., then feed 5 was metered in and the mixture was stirred until a homogeneous phase was present. Water was added to reach a solids content of 30% by weight.

The polymers as in example 8 and 10 were produced analogously to this.

Preparation of Copolymer as in Example 11

Polymer of MMA, MAA, AA and urethane diacrylate (Laromer®UA 19T) in the weight ratio 74:12:12:2

| Initial charge | 327 g | dem. water |
| | 200 g | ethanol |
| | 35 g | feed 1 |
| | 5 g | feed 2 |
| Feed 1 | 296 g | methyl methacrylate |
| | 48 g | MAA |
| | 48 g | AA |
| | 8 g | Laromer ® UA 19T |
| | 105 g | ethanol |
| Feed 2 | 58 g | ethanol |
| | 3.9 g | Wako ® V59 |
| Feed 3 | 60 g | ethanol |
| | 2 g | tert-butyl perpivalate |
| Feed 4 | 55 g | AMP |
| | 55 g | water |
| Feed 5 | 400 g | ethanol |

The initial charge was heated to 75° C. under a nitrogen atmosphere. Feed 1 was added over the course of 4 hours and feed 2 was added over the course of 5 hours. The polymer solution was then stirred at 78° C. for a further 2 hours. Feed 3 was then metered in over 30 min and the solution was then stirred for a further 4 hours at 80° C. Finally, the mixture was neutralized by adding feed 4 over 30 min. At a bath temperature of 120° C., ethanol was distilled off until an internal temperature of 85° C. had been reached. Distillation was then carried out with steam until an internal temperature of about 100° C. had been reached. Finally, the mixture was cooled to about 40° C., then feed 5 was metered in and the mixture was stirred until a homogeneous phase was present. Water was added to reach a solids content of 30% by weight.

The polymers as in example 12 were produced analogously to this.

Preparation of Copolymer as in Example 13

| Feed 1 | 657 g | methyl methacrylate |
| | 180 g | methacrylic acid |
| | 45 g | acrylic acid |
| | 18 g | Laromer ® UA 19 T |
| Feed 2 | 23 g | tert-butyl peroctoate |
| | 1015 g | ethanol cosm. |
| | 405 g | dem. water |

In a 5 l stainless steel reactor, 45 g of feed 1 were mixed with 450 g of cosmetic ethanol and 180 g of dem. water as initial charge. This initial charge was pressurized 3 times with a nitrogen atmosphere (5.0 bar) and then heated to 90° C. at 0.5 bar. 72.20 g of feed 2 were then added. After 10 min, feeds 1 and 2 were started together. Feed 1 was metered in over 3 hours and feed 2 was metered in over 4 hours at 90° C. under autogenous pressure. The reaction mixture was further polymerized for 2 hours at 90'C under autogenous pressure. Feed 3 (3.44 g of tert-butyl peroctoate, 43.00 g of ethanol cosm., 17.00 g of dem. water) was then metered in over 30 minutes and the mixture was afterpolymerized at 90° C. for 2 hours under autogenous pressure. Feed 4 (3.44 g of tert-butyl peroctoate, 43.00 g of ethanol cosm., 17.00 g of dem. water) was then metered in over 30 minutes and the mixture was afterpolymerized again at 90° C. for 2 hours under autogenous pressure.

Preparation of Copolymer as in Example 14

| Feed 1 | 2100.0 g | methyl methacrylate (MMA) |
| | 269.00 g | methacrylic acid (MAA) |
| | 269.00 g | acrylic acid (AA) |
| | 54.00 g | urethane acrylate A (UA A) |
| | 874.00 g | isopropanol |
| | 270.00 g | dem. water (dem. = completely demineralized) |
| Feed 2 | 40.00 g | Wako ® V-59 |
| | 360.00 g | isopropanol |

As initial charge, 190.00 g of feed 1 were mixed with 3500.0 g of isopropanol and 1075.0 g of dem. water in a 15 l stainless steel reactor. This initial charge was pressurized 3 times with a nitrogen atmosphere (5.0 bar) and then heated to 85° C. at 0.5 bar. 20.0 g of feed 2 were then added. After 10 minutes, feeds 1 and 2 were started together. Feed 1 was metered in over 3 hours and feed 2 was metered in over 4 hours at 85° C. under autogenous pressure. The reaction mixture was further polymerized for 2 hours at 85° C. under autogenous pressure.

2000.0 g of the resulting solution (solids content of 31.5% by weight) were heated to a temperature of 110° C. under autogenous pressure, and feed 3 (1.90 g of tert-butyl peroctoate, 25.00 g of isopropanol) was metered in over 30 minutes and the mixture was afterpolymerized for 2 hours under autogenous pressure at 110° C. Feed 4 (1.90 g of tert-butyl peroctoate, 25.00 g of isopropanol) was then metered in over 30 minutes and the mixture was afterpolymerized for a further 2 hours under autogenous pressure at 110'C.

900.00 g of the resulting solution (solids content of 30.0% by weight) were diluted with 96.0 g of dem. water and partially neutralized with 41.70 g of 2-amino-2-methyl-1-propanol and subjected to steam distillation. The mixture was then diluted with cosm. ethanol to a solids content of about 30.8% by weight. The resulting solution comprised about 1.3% by weight of isopropanol.

Preparation of Copolymer as in Example 15

| Feed 1 | 2100.0 g | methyl methacrylate (MMA) |
|---|---|---|
|  | 269.00 g | methacrylic acid (MAA) |
|  | 269.00 g | acrylic acid (AA) |
|  | 54.00 g | urethane acrylate A (UA A) |
|  | 874.00 g | isopropanol |
|  | 270.00 g | dem. water |
| Feed 2 | 40.00 g | Wako ® V-59 |
|  | 360.00 g | isopropanol |

As initial charge, 190.00 g of feed 1 were mixed with 3500.0 g of isopropanol and 1075.0 g of dem. water in a 15 l stainless steel reactor. This initial charge was pressurized 3 times with a nitrogen atmosphere (5.0 bar) and then heated to 85° C. at 0.5 bar. 20.0 g of feed 2 were then added. After 10 minutes, feeds 1 and 2 were started together. Feed 1 was metered in over 3 hours and feed 2 was metered in over 4 hours at 85° C. under autogenous pressure. The reaction mixture was further polymerized for 2 hours at 85° C. under autogenous pressure.

1815.0 g of the resulting solution were diluted with 355.0 g of dem. water in a 5 l stainless steel reactor and heated to a temperature of 90° C. under autogenous pressure, and feed 3 (1.70 g of sodium peroxodisulfate, 25.0 g of dem. water) was metered in over 30 minutes and the mixture was afterpolymerized for 2 hours at 90° C. under autogenous pressure. Subsequently, feed 4 (1.70 g of sodium peroxodisulfate, 25.0 g of dem. water) was metered in over 30 minutes and the mixture was afterpolymerized again for 2 hours at 90° C. under autogenous pressure.

900.00 g of the resulting solution (solids content of 30.0% by weight) were diluted with 96.0 g of dem. water, partially neutralized with 41.70 g of 2-amino-2-methyl-1-propanol and subjected to steam distillation. The mixture was then diluted with cosm. ethanol to a solids content of about 29.7% by weight. The odorless solution comprised 0.4% isopropanol.

Preparation of Copolymer as in Example 16

| Feed 1 | 234.0 g | methyl methacrylate |
|---|---|---|
|  | 30.00 g | methacrylic acid |
|  | 30.00 g | acrylic acid |
|  | 100.00 g | ethanol cosm. |
|  | 6.00 g | urethane acrylate A |
| Feed 2 | 6.0 g | Wako ® V-59 |
|  | 412.50 g | ethanol cosm. |
|  | 68.40 g | dem. water |

As initial charge, 15.0 g of feed 1 and 24.3 g of feed 2 were mixed with 171.50 g of cosmetic ethanol and 28.60 g of dem. water in a 2 l glass reactor. This initial charge was heated to reflux under a nitrogen atmosphere. After reaching the reflux temperature, feeds 1 and 2 were started together. Feed 1 was metered in over 3 hours under reflux and feed 2 was metered in over 4 hours under reflux. The reaction mixture was further polymerized for 2 hours under reflux. Then, feed 3 (1.50 g of tert-butyl perpivalate, 3.0 g of dem. water and 17.0 g of ethanol cosm.) were metered in over 30 minutes and the mixture was afterpolymerized under reflux for 2 hours. Subsequently, feed 4 (1.50 g of tert-butyl perpivalate, 3.0 g of dem. water and 17.0 g of ethanol cosm.) was metered in over 30 minutes and the mixture was afterpolymerized under reflux for a further 2 hours.

Preparation of Copolymer as in Example 17

| Feed 1 | 234.0 g | methyl methacrylate |
|---|---|---|
|  | 30.00 g | methacrylic acid |
|  | 30.00 g | acrylic acid |
|  | 6.00 g | urethane acrylate A |
| Feed 2 | 6.0 g | Wako ® V-59 |
|  | 412.50 g | ethanol cosm. |

As initial charge, 15.0 g of feed 1 and 21.0 g of feed 2 were mixed with 171.50 g of cosmetic ethanol and 103.0 g of dem. water in a 2 l glass reactor. This initial charge was heated to reflux under a nitrogen atmosphere. After reaching the reflux temperature, feeds 1 and 2 were started together. Feed 1 was metered in over 3 hours under reflux and feed 2 was metered in over 4 hours under reflux. The reaction mixture was further polymerized for 2 hours under reflux. Then, feed 3 (1.50 g of tert-butyl perpivalate and 17.0 g of ethanol cosm.) was metered in over 30 minutes and the mixture was afterpolymerized under reflux for 2 hours. Subsequently, feed 4 (1.50 g of tert-butyl perpivalate and 17.0 g of ethanol cosm.) was metered in over 30 minutes and the mixture was afterpolymerized for a further 2 hours under reflux.

Preparation of Copolymer as in Example 18

| Feed 1 | 2100.0 g | methyl methacrylate (MMA) |
|---|---|---|
|  | 269.00 g | methacrylic acid (MAA) |
|  | 269.00 g | acrylic acid (AA) |
|  | 54.00 g | urethane acrylate A (UA A) |
|  | 640.00 g | isopropanol |
|  | 500.00 g | dem. water |
| Feed 2 | 40.00 g | Wako ® V-59 |
|  | 360.00 g | isopropanol |

As initial charge, 190.00 g of feed 1 were mixed with 3300.0 g of isopropanol and 1300.00 g of dem. water in a 15 l stainless steel reactor. This initial charge was pressurized 3 times with a nitrogen atmosphere (5.0 bar) and then heated to 85° C. at 0.5 bar. 20.0 g of feed 2 were then added. After 10 minutes, feeds 1 and 2 were started together. Feed 1 was metered in over 3 hours and feed 2 was metered in over 4 hours at 80° C. under autogenous pressure. The reaction mixture was further polymerized for 2 hours at 85° C. under autogenous pressure.

1800.00 g of the resulting solution (solids content of 31.5% by weight) was diluted with 280.00 g of dem. water. Then, the temperature was increased under autogenous pressure to 105° C. and feed 3 (1.70 g of sodium peroxodisulfate, 22.50 g of dem. water) was metered in over 30 minutes and the mixture was afterpolymerized for 2 hours under autogenous pressure at 105° C. Subsequently, feed 4 (1.70 g of sodium peroxodisulfate, 22.50 g of dem. water) was metered in over 30 minutes and the mixture was afterpolymerized for a further 2 hours under autogenous pressure at 105° C. 900.00 g of the resulting solution (solids content of 30.0% by weight) were partially neutralized with 41.70 g of 2-amino-2-methyl-1-propanol and subjected to steam distillation. The mixture was then diluted with ethanol cosm. to a solids content of 25.0%. The odorless solution comprised 0.5% by weight of isopropanol.

Preparation of Copolymer as in Example 19

| Feed 1 | 891.6 g | methyl methacrylate |
|---|---|---|
|  | 114.3 g | methacrylic acid |
|  | 114.3 g | acrylic acid |
|  | 22.9 g | urethane acrylate A |
|  | 272.0 g | isopropanol |
|  | 307.8 g | dem. water |
| Feed 2 | 14.3 g | Wako ® V-59 |
|  | 103.0 g | isopropanol |

As initial charge, 86.1 g of feed 1 were mixed with 1018.3 g of isopropanol and 702.5 g of dem. water in a 15 l stainless steel reactor. This initial charge was pressurized 3 times with a nitrogen atmosphere (5.0 bar) and then heated to 85° C. at 0.5 bar. 5.9 g of feed 2 were then added. After 10 minutes, feeds 1 and 2 were started together. Feed 1 was metered in over 3 hours and feed 2 was metered in over 4 hours at 85° C. under autogenous pressure. The reaction mixture was further polymerized for 2 hours at 85° C. under autogenous pressure.

Then, 134.9 g of dem. water were added and the temperature was increased to 110° C. under autogenous pressure. Feed 3 (3.4 g of sodium peroxodisulfate, 44.6 g of dem. water) was metered in over 45 minutes and the mixture was afterpolymerized for 2 hours at 110° C. under autogenous pressure. Subsequently, feed 4 (3.4 g of sodium peroxodisulfate, 44.6 g of dem. water) was metered in over 45 minutes and the mixture was afterpolymerized again for 2 hours at 110° C. under autogenous pressure.

The resulting solution was partially neutralized with 70.0 g of 2-amino-2-methyl-1-propanol (95%) and diluted with 505 g of water, then the mixture is subjected to steam distillation. The mixture was then partially neutralized with 105.8 g of 2-amino-2-methyl-1-propanol (95%) and diluted with ethanol cosm. and water to a solids content of 34.3% by weight.

Determination of the K Value

The K values of the copolymers were measured in accordance with Fikentscher, Cellulosechemie, [Cellulose chemistry], vol. 13, pp. 58 to 64 (1932) at 25° C. in N-methylpyrrolidone (NMP) or ethanol solution and are a measure of the molecular weight. The respective solutions of the polymers comprised in each case 1 g of polymer in 100 ml of solution. Measurement was made in a micro-Ubbelohde capillary type M Ic from Schott.

| Copolymer | t-BA | EMA | MMA | SMA | MAA | AA | VP | NtB-EMA | DMA EMA | UDA | Si-UA | Alcohol/water (wt. ratio) | K value |
|---|---|---|---|---|---|---|---|---|---|---|---|---|---|
| 1 | 75 |  |  |  | 20 | 5 |  |  |  |  |  | EtOH:H$_2$O 2.5:1 | 37.4 |
| 2 |  | 75 |  |  | 15 | 10 |  |  |  |  |  | EtOH:H$_2$O 2.5:1 | 35.6 |
| 3 | 72 |  |  | 3 | 25 |  |  |  |  |  |  | EtOH:H$_2$O 3.5:1 | 36.1 |
| 4 |  |  | 73 |  | 12 | 12 |  |  | 3 |  |  | iPrOH:H$_2$O 2.7:1 | 32.5 |
| 5 | 52 |  |  |  | 3 |  | 27 | 18 |  |  |  | EtOH:H$_2$O 2.5:1 | 36.6 |
| 6 | 50 |  |  |  | 18 | — | 27 | 5 |  |  |  | EtOH:H$_2$O 2.5:1 | 36.9 |
| 7 | 50 |  |  |  |  |  | 30 | 20 |  |  |  | EtOH:H$_2$O 2.5:1 | 38.6 |
| 8 |  |  | 74 |  | 12 | 12 |  |  |  |  | 2* | iPrOH:H$_2$O 2.7:1 | 33.3 |
| 9 | 72 | — | — | 1 | 25 |  |  |  |  |  | 2 | EtOH:H$_2$O 3.5:1 | 37.2 |
| 10 | — | — | 76 | — | 11 | 11 |  |  |  |  | 2 | iPrOH:H$_2$O 2.7:1 | 32.9 |
| 11 |  |  | 74 |  | 12 | 12 |  |  |  |  | 2* | EtOH:H$_2$O 1.3:1 | 42.5 |
| 12 | — | — | 76 | — | 11 | 11 |  |  |  |  | 2 | EtOH:H$_2$O 1.3:1 | 44.7 |
| 13 | — | — | 73 |  | 20 | 5 |  |  |  |  | 2* | EtOH:H$_2$O 2.5:1 | 36.6 |
| 14 | — | — | 78 | — | 10 | 10 |  |  |  |  | 2** | iPrOH:H$_2$O [1]: 3.5:1 [2]: 1.2:1 | 33.1 |
| 15 | — | — | 78 | — | 10 | 10 |  |  |  |  | 2** | iPrOH:H$_2$O [1]: 3.5:1 [2]: 1.4:1 | 33.1 |
| 16 | — | — | 78 | — | 10 | 10 |  |  |  |  | 2** | EtOH:H$_2$O 5.5:1 |  |

-continued

| Copolymer | t-BA | EMA | MMA | SMA | MAA | AA | VP | NtB-EMA | DMA EMA | UDA | Si-UA | Alcohol/water (wt. ratio) | K value |
|---|---|---|---|---|---|---|---|---|---|---|---|---|---|
| 17 | — | — | 78 | — | 10 | 10 | | | | 2** | | EtOH:H₂O 5.3:1 | |
| 18 | — | — | 78 | — | 10 | 10 | | | | 2** | | iPrOH:H₂O [1]: 2.5:1 [2]: 1.2:1 | 34.7 |
| 19 | | | 78 | — | 10 | 10 | | | | 2** | | iPeOH:H₂O [1]: 1.3:1 [2]: 1.1:1 | 31.0**** |

*Laromer ®UA 19T: likewise suitable polymers were obtained by using a urethane diacrylate of PEG-1000 (4.5 mol), neopentyl glycol (1 mol), 1-butylaminoethyl methacrylate (1 mol) and IPDI (6 mol) (prepared analogously to DE 198 38 825) instead of Laromer ®UA 19T.
**Urethane acrylate A
***Weight ratio of alcohol to water in the solvent during the main polymerization [1], and the after polymerization [2]
****K value measured in 1% strength by weight ethanolic solution

| | | | | | | | Residual monomer content | | |
|---|---|---|---|---|---|---|---|---|---|
| Polymer | MMA [%]* | MAA [%]* | AA [%]* | Urethane [%]* | K value | Initiator | Water [%]* | MMA [mg/kg]** | MAA [mg/kg]** | AA [mg/kg]** |
| 16 | 78 | 10 | 10 | Urethane acrylate A 2 | | V59[1]/TBPP[2] | 14[1]/[2] | | | |
| 17 | 78 | 10 | 10 | Urethane acrylate A 2 | | V59[1]/TBPP[2] | 15[1]/[2] | | | |
| 14 | 78 | 10 | 10 | Urethane acrylate A 2 | 33.3 | V59[1]/TBPO[2] | 15[1]/[2] | 4 | 20 | 70 |
| 13 | 73 | 20 | 5 | Laromer ®UA 19T 2 | 36.6 | TBPO[1]/[2] | 20[1]/[2] | 190 | 60 | 40 |
| 15 | 78 | 10 | 10 | Urethane acrylate A 2 | 33.3 | V59[1]/NaPS[2] | 15[1] 30[2] | 15 | 20 | 190 |
| 18 | 78 | 10 | 10 | Urethane acrylate A 2 | 34.7 | V59[1]/NaPS[2] | 30[1] 46[2] | — | — | 90 |
| 19 | 78 | 10 | 10 | Urethane acrylate A 2 | 31.0 | V59[1]/NaPS[2] | 42[1] 48[2] | 3 | 11 | 16 |

[1] Main polymerization
[2] After polymerization
*[%]: % by wt.
**[mg/kg]: mg of residual monomer per kg of the total polymerization mixture

The invention claimed is:

1. A method of producing polymers which comprise, in copolymerized form, a) at least 50% by weight of olefinically unsaturated compounds selected from the group consisting of $C_1$-$C_{18}$-alkyl (meth)acrylates and b) at least a further monomer which is an olefinically unsaturated free-radically polymerizable compound containing urethane groups, by free-radical polymerization in solution, in an alcohol-comprising solvent which, based on the solvent, comprises 5 to 50% by weight of water, wherein the polymerization of a polymerization mixture comprising a) and b) in solution is carried out until a residual monomer content of at most 10% by weight is achieved, based on the solids content of the polymerization mixture, in the presence of at least one ethanol-soluble initiator, and a subsequent further polymerization of the polymerization mixture is carried out in the presence of at least one water-soluble initiator.

2. The method according to claim 1, wherein the solvent comprises water in the range from 15 to 45% by weight.

3. The method according to claim 1, wherein the solvent comprises alcohol in the range from 55 to 85% by weight.

4. The method according to claim 1, wherein the alcohol is selected from the group consisting of: ethanol, isopropanol and mixtures thereof.

5. The method according to claim 1, wherein a) is selected from the group consisting of: methyl (meth)acrylate, ethyl (meth)acrylate, n-butyl (meth)acrylate, isobutyl (meth)acrylate, tert-butyl (meth)acrylate and mixtures thereof.

6. The method according to claim 1, wherein the ethanol-soluble polymerization initiator is selected from the group consisting of: ethanol-soluble diazo and peroxide compounds.

7. The method according to claim 1, wherein the ethanol-soluble polymerization initiator is selected from the group consisting of: benzoyl peroxide, tert-amyl peroxipivalate, 2,2'-azobis(4-methoxy-2,4-dimethylvaleronitrile), 2,2'-azobis(2,4-dimethylvaleronitrile), dimethyl 2,2'-azobis(2-methylpropionate), 2,2'-azobis(2-methylbutyronitrile), 1,1'-azobis(cyclohexane-1-carbonitrile), 2,2'-azobis[N-(2-propenyl)-2-methylpropionamide], 1-[(cyano-1-methylethyl)azo] formamide, 2,2'-azobis(N-butyl-2-methylpropionamide), and 2,2'-azobis(N-cyclohexyl-2-methyl-propionamide).

8. The method according to claim 1, wherein the temperature at which the polymerization is carried out is in the range from 30 to 120° C.

9. The method according to claim 1, wherein, following the polymerization, the alcohol used as solvent is removed by distillation.

10. The method according to claim 9, wherein the polymer is neutralized in a range from 20% to 100% before the distillation.

11. The method according to claim 2, wherein the solvent comprises alcohol in the range from 55 to 85% by weight.

12. The method according to claim 2, wherein the alcohol is selected from the group consisting of: ethanol, isopropanol and mixtures thereof.

13. The method according to claim 3, wherein the alcohol is selected from the group consisting of: ethanol, isopropanol and mixtures thereof.

14. The method according to claim 2, wherein a) is selected from the group consisting of: methyl (meth)acrylate, ethyl (meth)acrylate, n-butyl (meth)acrylate, isobutyl (meth)acrylate, tert-butyl (meth)acrylate and mixtures thereof.

15. The method according to claim 3, wherein a) is selected from the group consisting of: methyl (meth)acrylate, ethyl (meth)acrylate, n-butyl (meth)acrylate, isobutyl (meth)acrylate, tert-butyl (meth)acrylate and mixtures thereof.

16. The method according to claim 4, wherein a) is selected from the group consisting of: methyl (meth)acrylate, ethyl (meth)acrylate, n-butyl (meth)acrylate, isobutyl (meth)acrylate, tert-butyl (meth)acrylate and mixtures thereof.

17. The method according to claim 2, wherein the ethanol-soluble polymerization initiator is selected from the group consisting of: ethanol-soluble diazo and peroxide compounds.

18. The method according to claim 3, wherein the ethanol-soluble polymerization initiator is selected from the group consisting of: ethanol-soluble diazo and peroxide compounds.

* * * * *